United States Patent
Vago

[11] Patent Number: 5,178,134
[45] Date of Patent: Jan. 12, 1993

[54] ULTRASONIC TREATMENT OF ANIMALS

[75] Inventor: Robert E. Vago, Bettendorf, Iowa

[73] Assignee: Malmros Holding, Inc., Morton Grove, Ill.

[21] Appl. No.: 753,008

[22] Filed: Aug. 23, 1991

Related U.S. Application Data

[60] Continuation of Ser. No. 726,948, Jul. 8, 1991, abandoned, which is a division of Ser. No. 322,128, Mar. 10, 1989, Pat. No. 5,048,520, which is a continuation-in-part of Ser. No. 175,936, Mar. 30, 1988, Pat. No. 4,942,868.

[51] Int. Cl.$^5$ .................................. A61B 17/22
[52] U.S. Cl. ...................... 128/24 AA; 128/660.03
[58] Field of Search ............ 128/24 AA, 660.03, 328; 604/22

[56] References Cited

U.S. PATENT DOCUMENTS

| | | | |
|---|---|---|---|
| 3,585,991 | 6/1971 | Balamuth | 128/24 AA |
| 4,216,766 | 8/1980 | Duykers et al. | 128/24 AA |
| 4,787,394 | 11/1988 | Ogura | 128/660.03 |
| 4,905,671 | 3/1990 | Senge et al. | 128/24 AA |
| 4,979,500 | 12/1990 | Hassler et al. | 128/660.03 |

Primary Examiner—William E. Kamm
Assistant Examiner—Geroge Manuel
Attorney, Agent, or Firm—Vincent L. Carney

[57] ABSTRACT

To provide ultrasonic treatment of animals, ultrasonic waves in a frequency range of between 15 kilohertz and 100 kilohertz are applied to water in a tube with a power density between 0.1 and 5 watts per square centimeter. The equipment is able to apply ultrasonic waves with at least two power densities in the vicinity of the portion of the animal with one of said power densities being more than 15 watts per square meter for sterilizing the water before the patient enters the tube and the other being less than 15 watts per square meter.

6 Claims, 5 Drawing Sheets

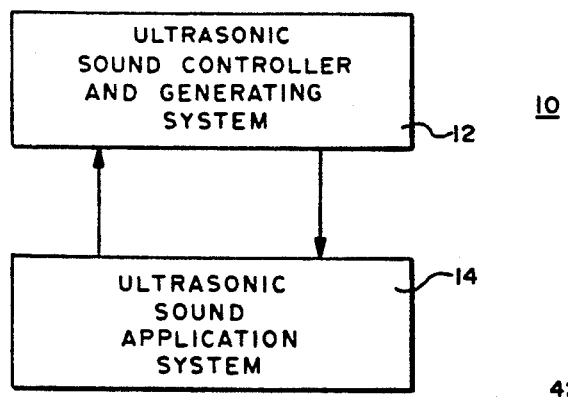
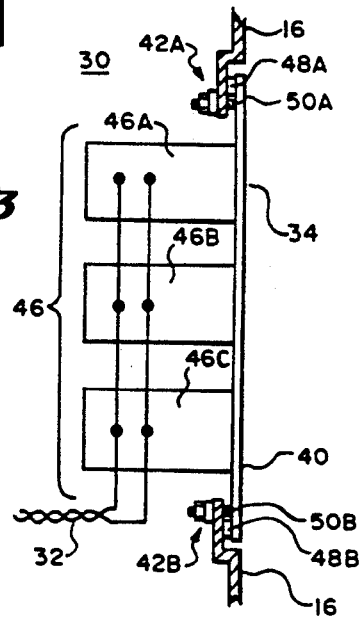
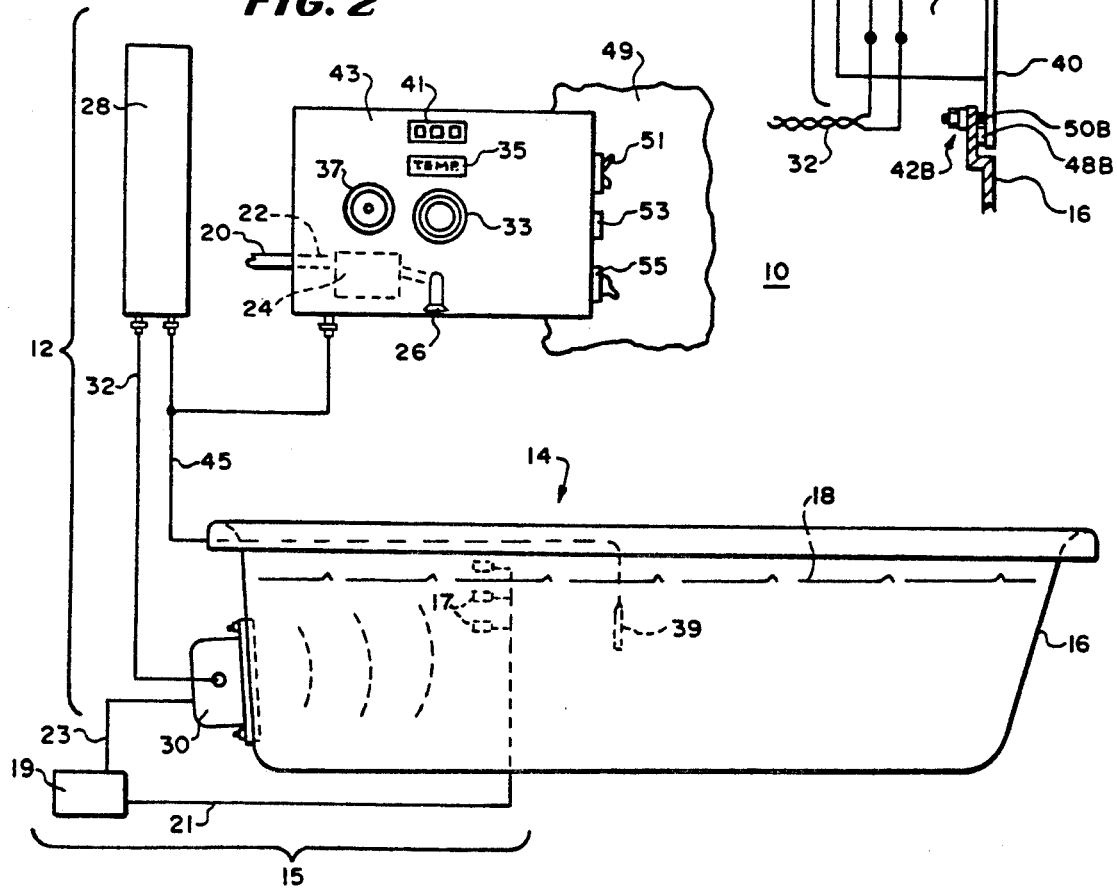

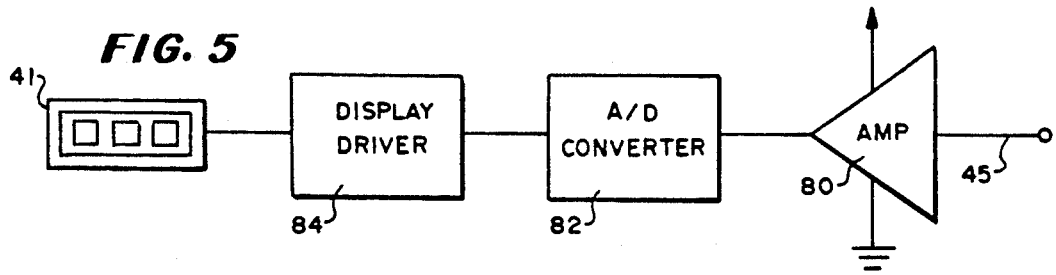
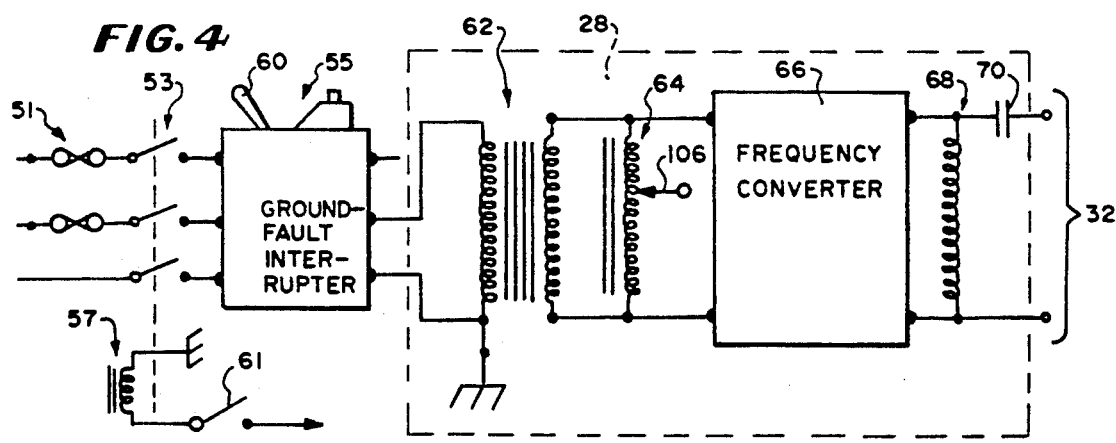
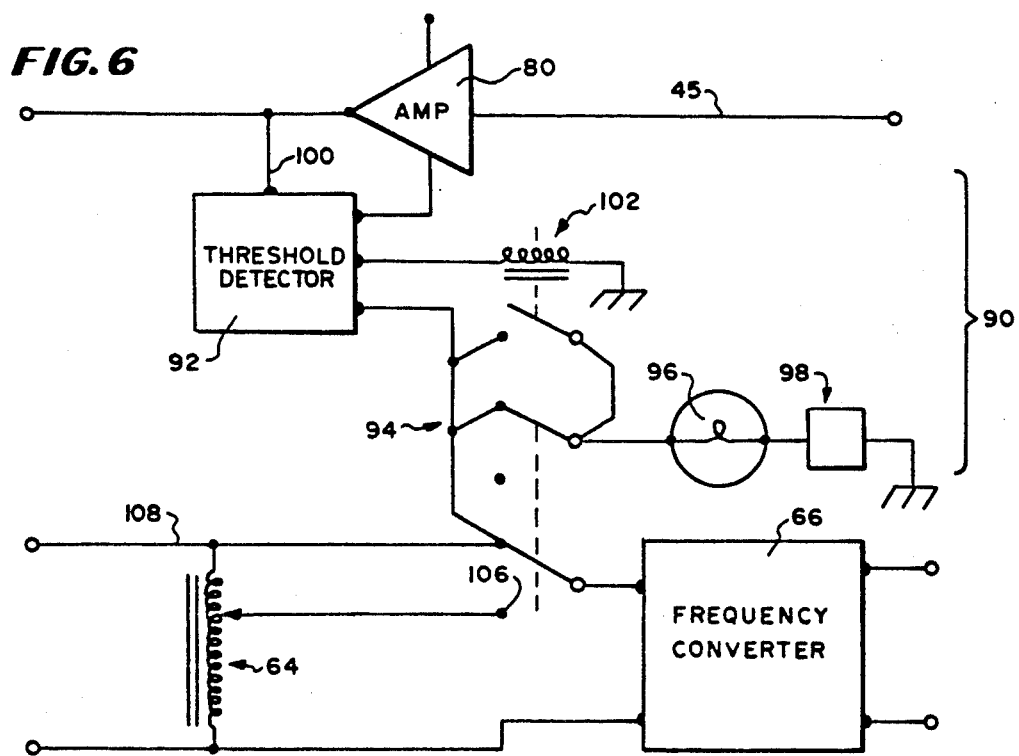

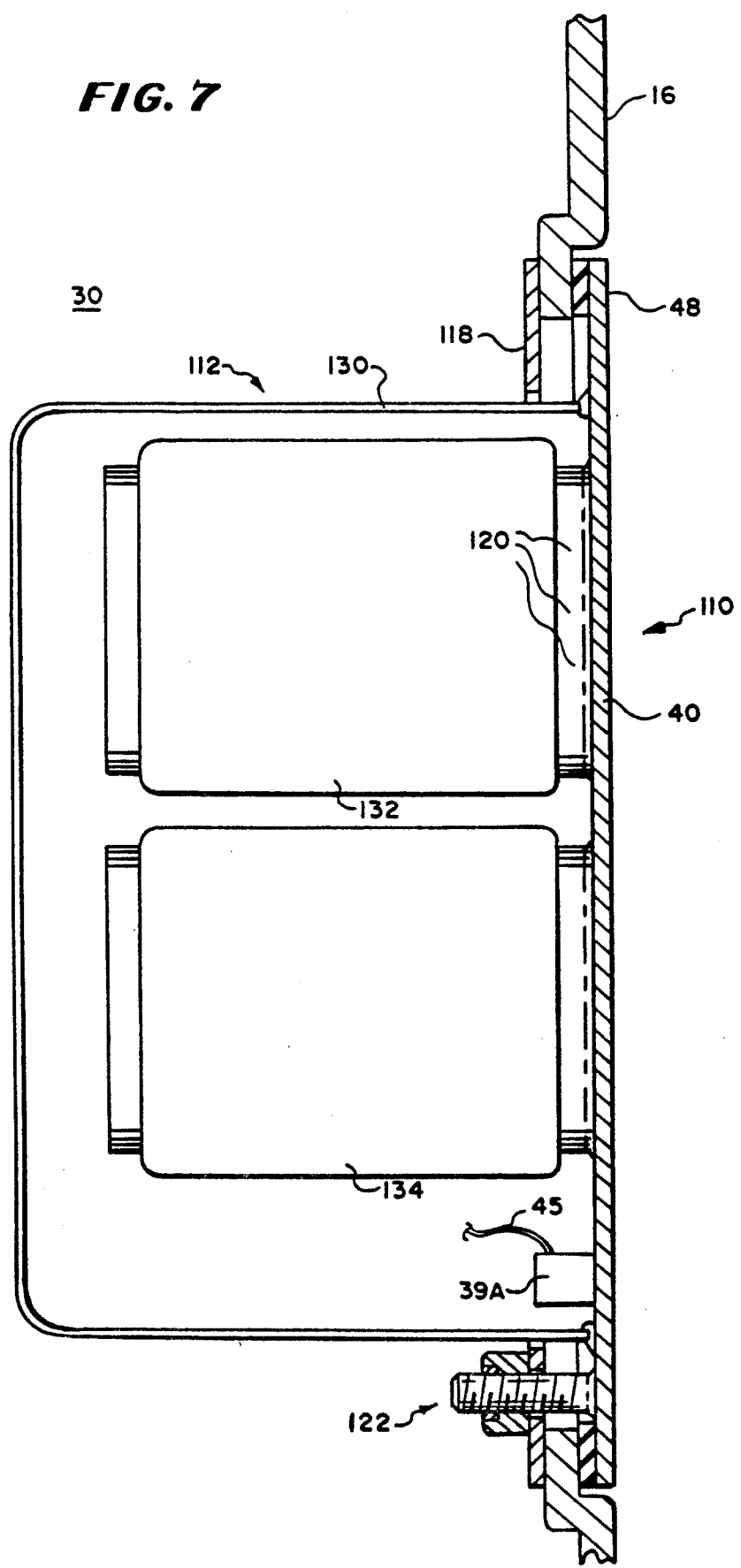

ULTRASONIC TREATMENT OF ANIMALS

RELATED CASES

This application is a continuation of application Ser. No. 07/726,948, filed July 8, 1991, now abandoned which is a division of application Ser. No. 07/322,128, filed Mar. 10, 1989, now U.S. Pat. No. 5,048,520 which is a continuation-in-part of application 175,936 filed Mar. 30, 1988, now U.S. Pat. No. 4,942,868, in the name of Robert Edward Vago for ULTRASONIC TREATMENT OF ANIMALS and assigned to the same assignee as this application.

BACKGROUND OF THE INVENTION

This invention relates to methods and equipment for treating animals including humans with ultrasonic waves for purposes of hygiene and therapy such as for example cleaning, microbicidal and antifungal activity and the promotion of epithelial healing.

In one class of ultrasonic treatment, ultrasonic sound is applied to a working fluid by a transducer. The part of the animal to be treated is immersed in the working fluid and the transducer transmits vibrations in the ultrasonic range to that animal through the working fluid.

In one prior art type of ultrasonic treatment for humans of this class, ultrasonic sound is applied to patients in a range of power levels of from 0 to 5 watts per square centimeter. It is generally used for stiff joints and muscular disorders. Other examples of treatment using ultrasound are provided in U.S. Pat. No. 4,501,151 to Christman, issued Feb. 26, 1985, for ULTRASONIC THERAPY APPLICATOR THAT MEASURES DOSAGE; U.S. Pat. No. 3,499,436 to Balamuth, issued Mar. 10, 1970, for METHOD AND APPARATUS FOR TREATMENT OF ORGANIC STRUCTURES WITH COHERENT ELASTIC ENERGY WAVES; and U.S. Pat. No. 3,867,929 to Joyner et al., issued Feb. 25, 1975, for ULTRASONIC TREATMENT DEVICE AND METHODS FOR USING THE SAME; and West German Utility model G8714883.8.

The therapeutic treatment described in the prior art has several deficiencies, mainly arising from the failure to use appropriate frequencies and intensities of ultrasound. For example: (1) some frequencies and intensities increase the risk of overheating the underlying tissue of patients; and (2) some are not useable for hygienic purposes because the selected frequency is higher than desirable. Moreover, the prior art literature does not contemplate antiviral, antibacterial or antifungal activity and has not been applied in a manner to accomplish antiviral, antibacterial or antifungal activity in an effective manner.

It is known to clean parts of the body with the aid of ultrasonic waves transmitted through a liquid medium. For example, U.S. Pat. No. 2,970,073 to Prange, issued Jan. 31, 1961, for METHOD FOR ULTRASONIC SURGICAL CLEANING OF HUMAN BODY MEMBERS discloses the use of ultrasonic sound in a range of between 10 to 200 kilocycles per second in a solution of water, germicide and surfactant to cleanse a surgeons hands. This patent recommends powers below 5 watts per square centimeter and frequencies between 15 to 50 kilocycles per second.

Still another description of cleaning apparatus using ultrasound is provided in European patent application, publication no. 0049759 which describes the use of ultrasound and liquid to remove fingernail polish. In some embodiments, the frequencies are in the megahertz range extending from approximately ¼ megahertz to 3 megahertz and in others are above 80 kilocycles such as disclosed in U.S. Pat. No. 3,867,929.

This type of ultrasonic cleaning device has a disadvantage in that it is usable only with additives such as germicides in the case of U.S. Pat. No. 2,970,073 and nailpolish remover in the case of U.S. Pat. No. 3,316,922 or Offenlegungsschrift DE3238476 or European design patent G8714883.8.

The treatment of injured soft tissue and bone is known from Dyson et al. "Induction of Mast Cell Degranulation in Skin by Ultrasound", *IEEE Transaction on Ultrasonics, Ferroelectronics and Frequency Control*, vol. UFFC 31, n. 2, March 1986, pp. 194–201. However, this information has not been used in an integrated system for bathing and therapy.

SUMMARY OF THE INVENTION

Accordingly, it is an object of the invention to provide a novel apparatus for ultrasonic treatment of animals.

It is a further object of the invention to provide a novel method for ultrasonic treatment of animals.

It is a still further object of the invention to provide a novel technique for treating animals with ultrasonic waves which provide hygienic and therapeutic benefits without being irritating or harmful to the animals.

It is a still further object of this invention to utilize ultrasonic waves efficiently in a frequency range which is beneficial to animals.

In accordance with the above and further objects of the invention, apparatus for ultrasonic treatment includes a container holding a working liquid and means for generating vibrations in the working liquid in a frequency range and in a power range that are not irritating or harmful to animals, including humans, and yet which produce one or more beneficial effects, such as for example, cleaning or antimicrobial or therapeutic effects.

The container in the preferred embodiment is a bathtub but may be smaller such as for example a small container sufficient to immerse a part of the human body such as a foot. The frequency range and power are selected together to avoid transient cavitation that may harm the bather but yet produce sufficient linear cavitation for cleaning or to destroy certain microbes such as harmful bacteria or fungus on the skin and in the liquid within the container or to promote healing. In some embodiments, the linear cavitation is controlled to avoid a tendency to become non-linear. In such embodiments, the linear cavitation is stabilized by controlling the vibrations applied to the working liquid to compensate for shifts in cavitation that occur even with a stable applied vibration. One way of avoiding such instability is by applying an asymetric pressure wave.

The frequency that is used is in the range of frequencies between 15 and 100 kilohertz and the power density is less than 10 watts per square centimeter, although the cleaning efficiency begins to drop as the frequencies exceed 80 kilohertz and some detectable feeling is obtained from power density over 5 watts per square centimeter. To avoid standing waves and audible noise from subharmonic generation, the frequency is altered over a range and at a rate that prevents the forming of high intensity vibrations formed by reflected waves coinciding in time and space with other waves and to reduce lost energy by stable resonant vibrations at subharmonic frequencies. The preferred frequency is substantially 30 kilohertz and the preferred power density (SPTP) for bather exposure is 0.1 to 5.0 watts per square centimeter although variations may be made in the two to provide the desirable beneficial effect while avoiding harm to the bather. The sweep rate is periodic at substantially 120 hertz and covers a 1 kilohertz band centered at 30 kilohertz with an approximate 80 percent modulation.

To sterilize the water before bathing, the power density of the ultrasound is increased to a level sufficient to destroy microbes. The ultrasound is applied at a frequency selected for efficiency in destroying the microbes with the lowest power consistent with sterilization and with acceptable radiation levels of sound to the air. This power density (SPTP) is above 15 watts per square centimeter and at a frequency above 15 kilohertz but may be selected for the circumstances. Additives, such as detergents or antiseptics may be added but are not needed for sterilization if sufficient sonic intensity is used. Such additives may be added and lower sonic intensities used or lower time duration of the ultrasound to avoid harming the patiesnt while still killing pathogens. This procedure may also be used to sterilize inanimate objects in the liquid.

Generally in manufacturing a bath, the size of the container, the liquid, the frequencies of sound, and the power of transmission are selected to provide the cleaning, therapeutic or microbicidal benefits while avoiding deleterious effects. Although these factors are all considered during product design and use, the order of selection is generally: (1) the size of the container in connection with the purpose such as for a foot bath or for full bathing of a human or the like (2) the nature of the liquid, such as degassed water, water with a mild detergent or with a mild antiseptic; (3) the frequency or the sequence of different frequencies to be applied in connection with the purpose; and (4) the power or sequence of powers effective for the desired purpose. After a theoretical selection, the values are adjusted to avoid any observed undesirable effects such as standing waves or irritating sound transmission.

Unless special measures are taken, bathers perceive some sound which is not airborne nor generated in the water but is received through the body from the water. This sound, under some circumstances, may be irritating and should be attenuated, altered in frequency or eliminated.

To alter, attenuate or eliminate the perception of this sound, the vibrating plate or plates may be modified structurally or controlled electrically. They may be modified to reduce the transmission through the water of those subharmonics that may result in the undesirable sound received by the bather.

To modify the plates structurally, their shape or number or size or points of being driven are changed. The changes are made to modify the vibrational modes to more suitable modes.

To control the vibrating plates electrically in a way that avoids the perception of sound, the vibrations in the working fluid are sensed by a probe. The sensed vibrations are processed to remove the principal frequency, which in the preferred embodiment is 30 KHz, such as by filtering and fed back for control purposes. The sensed lower frequency subharmonics filtered from the sensed vibrations are used to cancel the exciting subharmonics being applied to the working fluid by adjusting the amplitude of the feedback circuit and subtracting the sensed subharmonics from the transducer exciting signal.

To permit power at levels for sterilization without or with additives, either: (1) special provisions must be made to energize the same transducers used for bathers in a different way; or (2) different or more transducers and vibrating plates must be used. For example, the transducer may be pulsed with high current pulsations to provide spurts of high intensity ultrasound with time between current pulses to permit cooling. In the alternative, multiple vibrations placed to avoid standing waves can be used.

The liquid is generally water and preferably degassed water with a mild detergent. The housing of the sound generator and the bath container wall are designed to absorb sound and thus reduce acoustical radiation, attenuation or other undesired effects. Precautions are taken to avoid risk of electric shock of a bather.

To use the ultrasonic treatment in accordance with the invention, water is degassed, a tub is filled with degassed water and a mild detergent is added. The patient is immersed in the water, or if desired, a single part of the body such as the foot is immersed in the water and ultrasonic sound is transmitted through the water. The sound is transmitted by applying oscillations to a magnetostrictive transducer which communicates with the water through an electrically insulative vibrating plate in the side of the tub to create vibrations at a selected frequency within a frequency range of 15 through 100 kilohertz and preferably at 30 kilohertz with a STPT power density of less than 15 watts per square centimeter and preferably 0.1 to 5.0 watts per square centimeter. In one embodiment, the intensity may be changed to a range between 80 and 16 milliwatts per square centimeter SATA (spacial-average, time-average) at one-quarter wavelength from the transducer.

For safety, a meter measures the power density so observers can determine if it is safe and automatic threshold devices reduce or shut power off should it become too large. Moreover, in some embodiments, a sensor detects a foreign object in the liquid during sterilization and shuts off or reduces the power to prevent harm to the object.

In one embodiment, cross contamination is avoided by increasing the power density in the working fluid to a level high enough to destroy microbes before and/or after use of the bathing system.

During use by a bather, some germicidal and fungicidal benefits are obtained by the low intensity ultrasound that is safe for the bather. This effect may be synergistically improved with additives that destroy pathogens and are brought into more ready contact with the pathogens by microstreaming induced by ultrasound.

During the inflamation period of wounds, the application of low frequency energy in the range of 15 to 100 kilohertz at intensities of between 1 and 5 watts per square centimeter promotes healing. The ultrasound is applied periodically such as for periods of between 5 minutes and 20 minutes at reasonable time intervals such as one or two times each day and results in reduced polymorphs indicating more effective action of the immune system or independent destruction of pathogens.

Similarly, during the rapid proliferation healing of wounds, periodic application of this ultrasound in substantially the same ultrasonic frequencies, intensities, time durations and number of repetitions each day promotes fiberblast development.

Because of these effects, it is possible to bathe animals or persons having wounds in a manner that aids in cleaning without damaging the wounds, and under some circumstances, even promoting healing. This is accomplished by immersing a bather with wounds for a number of times between once every two days and four times a day and for a time period selected to avoid increasing inflamation and retarding healing wherein the bather is cleaned while wound healing is aided. The number of times, time durations and repetition rate of bathing with sonically energized working fluid is selected by observing the wounds and reducing time in the ultrasound energized working fluid upon any one of irritation during bathing, increased inflammation after bathing or slow healing rate.

From the above description, it can be understood that the apparatus and method of this invention has several advantages over the prior art, such as: (1) it has hygienic, therapeutic and antimicrobial benefits while being harmless to animals; (2) it makes economical use of vibrating transducers by using attenuating water as a working fluid; and (3) it performs both cleaning and wound-healing while at the same time providing antiviral, antibacterial and antifungal activity in a manner making it suitable for treatment of certain particularly severe maladies such as severe burns.

DESCRIPTION OF THE DRAWINGS

The above noted and other features of the invention will be better understood from the following detailed description when considered with reference to the accompanying drawings, in which:

FIG. 1 is a block diagram of an ultrasonic treatment system in accordance with an embodiment of the invention;

FIG. 2 is a schematic diagram of a bathing system which is one form of the ultrasonic treatment system of FIG. 1;

FIG. 3 is a simplified schematic diagram of a transducer element positioned with respect to a container for working fluid in accordance with the invention;

FIG. 4 is a schematic diagram of an ultrasonic generator useful in the embodiment of FIG. 3;

FIG. 5 is a block diagram of a power density display forming a part of the embodiment of FIGS. 1 and 2;

FIG. 6 is a schematic circuit diagram of an embodiment of feedback circuit useful in practicing the invention;

FIG. 7 is a sectional view of a transducer assembly forming part of FIGS. 1 and 2;

DETAILED DESCRIPTION

Figure 8:
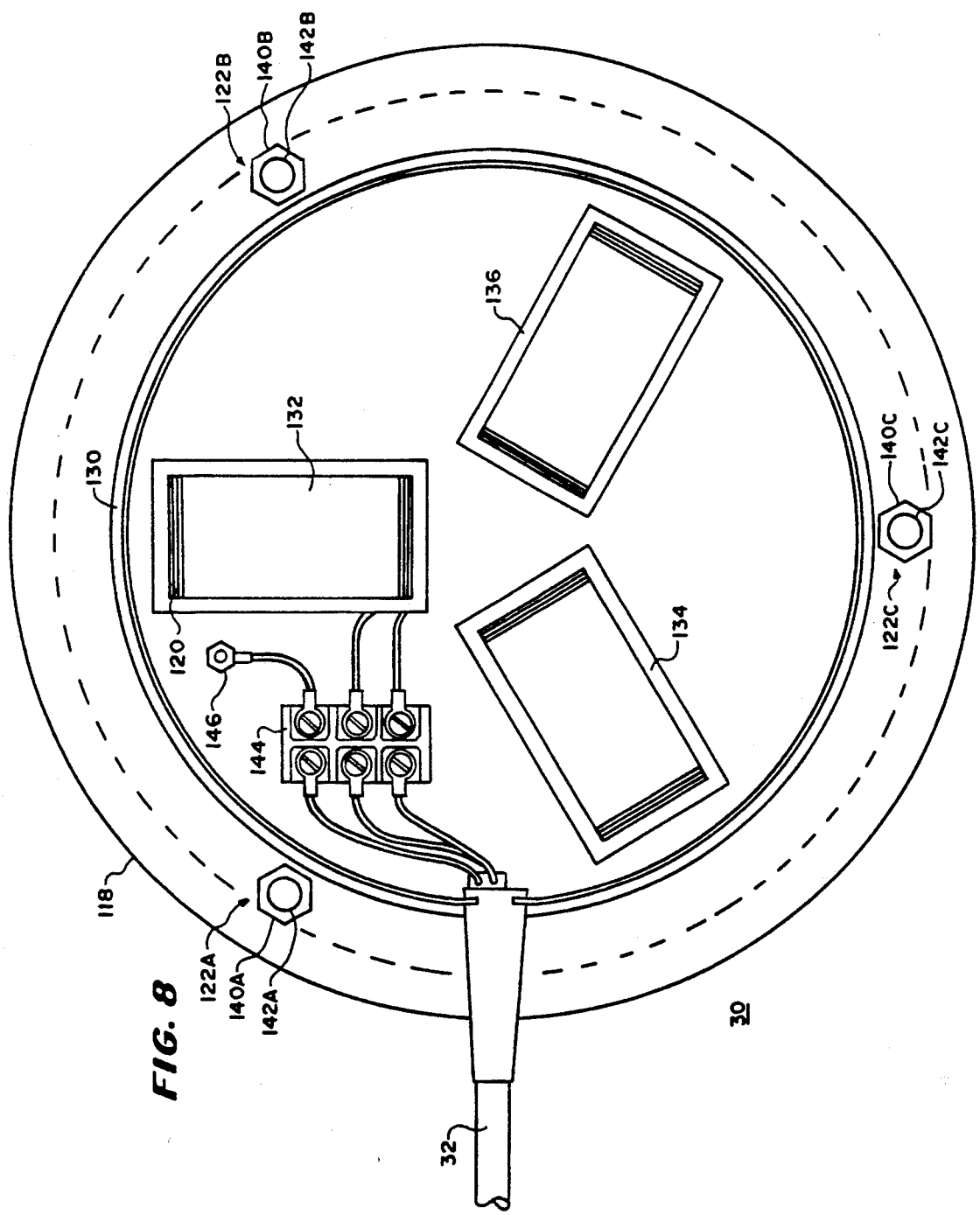
FIG. 8 is an elevational view of an internal portion of the transducer of FIG. 6.

In FIG. 1, there is shown a block diagram of an ultrasonic sound system 10 having an ultrasonic sound controller and generating system 12 and an ultrasonic sound application system 14 connected together to supply ultrasonic sound for hygienic, therapeutic and antimicrobial functions. The ultrasonic sound controller and generating system 12 is connected to and transmits signals to the ultrasonic sound application system 14, which may be a bathing system, to provide hygienic and therapeutic benefits to a bather.

In some embodiments, a transducer within the ultrasonic sound application system 14 supplies a feedback signal to the ultrasonic sound controller and generating system 12 for monitoring purposes. The ultrasonic sound system 10 may aid in cleaning, may provide epithelial healing for an animal and particularly for humans and at the same time be actively bacteriocidal, viricidal and fungicidal.

The frequency of the vibrations is maintained in a range within 15 and 100 kilohertz and the STPT power density is less than 15 watts per square centimeter, although the cleaning efficiency begins to drop as the frequencies exceed 80 kilohertz and some detectable feeling is obtained from an STPT power density over 5 watts per square centimeter. The preferred frequency is substantially 30 kilohertz and the preferred power density is 0.1 to 5.0 watts per square centimeter although variations may be made in the two to provide the desirable beneficial effect while avoiding harm to the bather.

Energy density (energy per unit area) and intensity (power density or power per unit area) of the ultrasound in this specification is described in terms of spacial-average temporal-average values (SATA), spacial-peak temporal-average values (SPTA), spacial-average temporal-peak values (SATP) or spacial-peak temporal-peak values (SPTP). Of course, these terms have their known meanings in the art so that peak values of energy or intensity are the maximum values occuring in a cycle and energy and power densities are described spacially because they occur at certain areas or temporal to indicate that they occur at a certain time. Similarly, the average values may either be the average values at a given location in given space or the average values at a certain time. In one embodiment, the power intensity is in a range from 80 mW (milliwatts) to 16 mW per square centimeter one-quarter wavelength from the transducer (SATA).

The frequency and intensity of the ultrasound is selected to avoid tissue damaging heating effects. By selected frequencies under 100 kilohertz, heat damage to tissue is avoided. Cavitation is the effect which causes beneficial effects and may cause harmful effects. Cavitation is maintained in a linear range and nonlinear transient cavitation is avoided because of the risk of damage being done during the peaks of the transient high-intensity sound. In linear cavitation, the bubble vibrates at the impressed frequency, growing and shrinking in size between certain size limits.

Because the intensity (power per unit area) varies both with time and space, the transmission of the ultrasound is designed to provide effective operation without damage in all of the regions where the bather may be. Linear cavitation or forming of microstreams of bubbles performs the cleaning operation and under some circumstances may aid in healing and in antimicrobial effects.

Variations caused by attenuation when a single source of sound is used is reduced by degassing the working fluid or water to remove the large bubbles (larger than 50 microns) which otherwise tend to cause attenuation of the sound as it is transmitted through the working fluid. The smaller voids or bubbles between 20 and 40 microns move back and forth in a process called microstreaming to perform a cleaning operation and to aid in therapy by a stimulation type of activity which seems to reduce the macrophages at wound surfaces. Thus, the lowest SPTP value which occurs adjacent to the bather must be sufficiently high for such microstreaming and the highest intensity (SPTP) must be below that which causes transient cavitation or nonlinear cavitation to injure the cells of a patient.

To sterilize the water before bathing, the power density of the ultrasound is increased to a level sufficient to destroy microbes. The ultrasound is applied at a frequency selected for efficiency in destroying the microbes with the lowest power consistent with sterilization and with acceptable levels of sound radiation to the air. This power density SPTP is above 15 watts per square centimeter and at a frequency above 15 kilohertz but may be selected for the circumstances. Additives, such as detergents or antiseptics may be added. This procedure may also be used to sterilize inanimate objects in the liquid. The higher intensity is obtained by using multiple plates or by pulsing the same transducers and plate to avoid a reduction in efficiency caused by heating effects in the transducer at a high power.

In FIG. 2, there is shown a schematic drawing of the ultrasonic sound system 10 showing one embodiment of ultrasonic sound controller and generating system 12 mounted to one type of ultrasonic sound application system 14. In this embodiment, the ultrasonic sound application system 14 includes a plastic bath tub 16 containing water as a working fluid 18 and a supply of water such as that available from the faucet 26 in a wall panel 49. In one embodiment, a control system 15 is connected to the bathing system to reduce or terminate high power density ultrasonic waves if a person intrudes into the body of water 18. The supply of water 20 is positioned for any preliminary processing necessary and for convenient transfer to the tub 16.

The tub 16 must be sufficiently strong to contain the body of water 18 and sufficiently large so that a human or other animal such as a pet may have the required portion of its body immersed in the body of water 18. In the preferred embodiment, the tub 16 is a bathtub but it may be a foot basin or pet bath or the like.

To supply degassed water, the supply of fluid includes a water pipe or the like 22 to receive water, a degasser 24 and a valve such as a faucet or the like 26 positioned so that water may flow through the water pipe 22 from a source such as a household source through the degasser 24 and into the tub 16 after degassing. There are many commercial degassers including those that work with a vacuum operating through a mesh or a membrane or the like and any such system is suitable.

The ultrasonic sound controller and generating system 12 includes an ultrasonic generator 28 for generating periodic electric signals and a transducer assembly 30 for converting the electric signals to vibrations that are transmitted through the body of water 18 for cleaning, epithelial therapy and microbicidal effects. The ultrasonic generator 28 receives power from the mains power source and may be adapted to utilize either 115 or 230 volt, 60 hertz input power or 50 hertz input power. It is electrically connected by cable to the transducer assembly 30 for supplying vibrations within a frequency range and power which is not irritating or harmful to the patient nor to persons nearby because of sound radiation from the transducer assembly or from water to the air.

In the preferred embodiment, a frequency of 30 kilohertz is used. The SPTP power density for degassed water at this frequency is approximately 0.1 to 5.0 watts per square centimeter but for partially degassed water any absolute value is lower by 0.1 watts per square centimeter and for somewhat gassy water the intensity is lower by 0.2 watts per square centimeter. The specific frequency need not be 30 Khz (kilohertz) but is preferred in the range of 20 Khz plus or minus 15 Khz.

To control the comfort of the patient within the ultrasonic sound system 10, the temperature of the water from the faucet 26 is controlled by mixing different proportions of cold and warm water as set by the dial 33 and indicated in the temperature gauge 35. Similarly, the power density emitted by the transducer assembly 30 is adjustable by the dial 37 and the power of the vibrations in the bath as measured by a transducer 39 is shown on the LED display 41.

To apply signals of the selected frequency and intensity to the ultrasound transducer assembly 30, the ultrasonic generator 28 is electrically connected to the ultrasound transducer assembly 30 by a cable 32 and both the ultrasonic generator 28 and control panel 43 are electrically connected to the transducer 39 to receive feedback signals through a cable 45. The control panel 43 also contains other normal electrical devices which are not part of the invention such as a ground fault interrupter 51, fuses 53 and a mains power switch 55.

Although in the embodiment of FIG. 2, the transducer 39 is positioned near the expected location of a bather, in the preferred embodiment, a transducer will be located in the assembly 30 on an inner plate described hereinafter and connected to the cable 45. The circuit will be calibrated at the factory using a transducer located at the expected location of a bather to obtain values corresponding to feedback signals from the transducer on the inner plate.

In some embodiments, a control system 15 includes a plurality of sensors 17 electrically connected to a detector 19 which in turn is connected to the ultrasonic generator 28 for control purposes. The sensors 17 are capacity sensors mounted to the tub 16 to detect an increase in the level of water due to the intrusion of a person into the water. Instead of capacity detectors which detect an increase in the level of the water, other types of detectors may be used including sonic detectors that detect a person near the surface of the water or heat detectors or the like. These detectors supply a signal to the ultrasonic generator 28 when the ultrasonic generator 28 is utilizing high power for sterilization purposes. It is intended to prevent a person from entering the tub while the high power is being applied to avoid harm.

For this purpose, the circuit 19 detects an increase in the level of water as a change in capacitance, differentiates the received signal and applies it to one input of an AND gate. The other input of the AND gate, if energized by the presence of high power signals, will de-energize the ultrasonic generator 28 so that the power is instantaneously eliminated. Instead of terminating the power, a resistance may be inserted in circuit with the electric signal from the ultrasonic generator 28 to reduce the power. These changes occur quickly before harm can be done to the patient.

Unless special measures are taken, bathers perceive some sound which is not airborne nor generated in the water but is received through the body from the water. This sound, under some circumstances, may be irritating and should be attenuated, altered in frequency or eliminated.

To alter, attenuate or eliminate the perception of this sound, the vibrating plate or plates may be modified structurally or controlled electrically. They may be modified to reduce the transmission through the water of those subharmonics that may result in the undesirable sound received by the bather.

To modify the plates structurally, their shape number or size or points of being driven are changed. The changes are made to modify the vibrational modes to more suitable modes.

To control the vibrating plates electrically in a way that avoids the perception of sound, the vibrations in the working fluid are sensed by a probe. The sensed vibrations are processed to remove the principal frequency, which in the preferred embodiment is 30 KHz, such as by filtering. The sensed lower frequency subharmonics filtered from the sensed vibrations are used to cancel the exciting subharmonics being applied to the working fluid by adjusting the amplitude of the feedback circuit and subtracting the sensed subharmonics from the transducer exciting signal.

To stabilize linear cavitation and thus avoid a tendency for the cavitation to become non-linear, the vibrations applied to the working liquid are controlled in such a way as to compensate for shifts in cavitation that occur even with a stable applied vibration. These shifts occur because the surface area of a bubble is slightly greater during expansion (negative pressure) cycles than compression (positive pressure) cycles. The gas diffusing out of a bubble during a compression cycle is less than the gas diffusing into a bubble during an expansion cycle so that for each successive cycle, the bubble increases in size. Over many cycles (typically 300 microseconds) a bubble can reach resonant size at which it can no longer sustain itself. The water rushes in and the bubble implodes.

Typically at implosion the temperature of the liquid surrounding the bubble is at 2100 degrees Celsius while the temperature of the vapor within the bubble reaches 5500 degrees Celsius. Correspondingly, the internal pressure can rise to 7500 pounds per square inch, which when in close proximity to the surface, will hurl a water jet towards the surface at 250 MPH. The implosion forces and shock waves not only remove contaminant but also erode surfaces.

One way of avoiding such instability is by applying an asymetric pressure wave. Since the size increase in a bubble is due to more gas being diffused into a bubble than is diffused out of a bubble, an asymetric pressure wave having an applied positive pressure higher than the applied negative pressure can equalize the amount of gas diffused into and out of a bubble. Normally in ultrasonic cleaning, a pressure wave of equal positive and negative amplitude is applied to stimulate cavitation because the desired result is normally non-linear cavitation. However, for the uses described herein, non-linear cavitation is not desired because non-linear cavitation events can be damaging to delicate surfaces. Instead, an alternative cleaning phenomenon known as microstreaming is created and maintained by stabilizing cavitation. Microstreaming relies upon interaction of thousands of linearly vibrating bubbles for its effect.

In microstreaming, between adjacent linearly vibrating bubbles, opposing eddy-currents are established in the aqueous medium and it is there opposing currents which serve to twist the contaminants free of a parent body. This scrubbing action is not violent and represents a virtually non-damaging cleaning mechanism for delicate surfaces.

The asymetric pressure wave is produced in the ultrasonic sound controller and generating system 12. To create and sustain microstreaming, the ultrasonic generator 28 forces the transducer to follow its electrical waveform. Normally, the applied waveform is typically sinusoidal of equal positive and negative amplitude. In the invention, a fixed D.C. bias is added during the positive going wave and subtracted during the negative going wave—positive meaning positive hydrodynamic pressure in the aqueous solution and negative meaning negative hydrodynamic pressure. The fixed D.C. bias is adjustable and may be controlled manually or automatically.

To control the asymetric pressure wave, the transducer 39 is connected to an oscilloscope to monitor the resulting pressure waveforms. Without non-linear cavitation being present, the oscilloscope wave outline is clean and free of pertubations. With non-linear cavitation being present, many spikes appear on the wave outline so when only linear cavitation is present, it is easily determined. This adjustment occurs normally during the factory calibration phase. The D.C. bias control is adjustable either manually or automatically to account for tolerances.

To permit power at levels for a sterilization without or with additives, either: (1) special provisions must be made to energize the same transducers used for a bather in a different way; or (2) different or more transducers and vibrating plates must be used. For example, the transducer may be pulsed with high current pulsations to provide spurts of high intensity ultrasound with time between current pulses to permit cooling. In the alternative, multiple vibrations placed to avoid standing waves can be used.

In FIG. 3, there is shown a schematic diagram of the ultrasound transducer assembly 30 electrically connected by the cable 32 to the ultrasonic generator 28 (FIG. 2). The ultrasound transducer assembly 30 includes an interface and a transducer body connected together so that the transducer body generates mechanical vibrations in a selected frequency range and imparts them to the interface which in turn imparts them to the body of water 18.

To generate vibrations, the transducer body includes three transducer elements 46A, 46B and 46C electrically connected to the cable 32 and in series with each other to vibrate in synchronism and thus impart vibrations to the interface. The transducers in the preferred embodiment are magnetostrictive transducers but other types of transducers may be utilized such as piezoelectric transducers or the like. Moreover, an electrically actuated transducer may be positioned near the ultrasonic generator 28 (FIG. 2) and separated from the interface if desirable, with a long acoustic coupling such as a pneumatic coupling being utilized to transfer vibrations to the interface and ultimately to the body of water 18.

To transmit vibrations to the working fluid, the interface includes a vibrating plate 40 and a plurality of fasteners two of which are shown at 42A and 42B to mount the vibrating plate 40 to the plastic container or bath tub 16. In the preferred embodiment, one side of the vibrating plate 40 is mounted to a housing for the ultrasound transducer assembly 30 and the other side is positioned to be in contact with the body of water 18 in a manner to be described hereinafter.

The fastener means 42A and 42B include corresponding studs 50A and 50B welded to the vibrating plate 40 and adapted to have threaded upon them corresponding nuts which compress corresponding gaskets 48A and 48B against the edges of the tub 16, with the main portion of the vibrating plate 40 being on one side of the tub 16 and the transducers on another side so that the vibrating plate 40 is moved by the transducers with respect to the wall of the tub 16 and compresses and decompresses the gaskets 48A and 48B without permitting fluid to leak therethrough.

To further reduce lost energy and possible irritating or harmful effects, the tub 16 (FIG. 2) is designed to reduce sound transmission to the air and standing waves within the water. As part of this design, the wall of the tub 16 material is a sound absorbant plastic which is particularly absorbent to the frequency of the transducers.

In FIG. 4, there is shown a schematic circuit diagram of a portion of the ultrasonic generator 28 connected to the ground fault interrupter 55 and fuses 51 through a mains power switch 53. The ground fault interrupter 55 may be of any suitable type containing a manual switch 60 and an internal switch triggered by current to ground of the order of 5 milliamperes to open the circuit. Suitable ground fault interrupters may be purchased from Arrow-Hart, under Model No. 9F2091MI. The mains power switch 53 may be manually controlled and is, in one embodiment, also controlled by a solenoid 57 to permit it to return to its normally open position when the power density in the ultrasonic sound application system 14 (FIG. 2) exceeds a preset limit in a manner to be described hereinafter.

The ultrasonic generator 28 includes an isolation transformer 62, an autotransformer 64, a frequency converter 66, an output matching inductor 68 and an output isolation capacitor 70. The isolation transformer 62 receives a 115 volts AC on its primary and conducts to the frequency converter 66 a reduced voltage under the control of the autotransformer 64 which may be adjusted to the potential applied to the frequency converter 66.

To generate 30 kilohertz cycles at a power under the control of the autotransformer 64, the frequency converter 66 may be of any suitable type, many of which are available on the market. In the preferred embodiment the frequency converter is a swept frequency generator having a carrier frequency of 30 Khz modulated at 100 to 120 hertz across a band of plus or minus one-half kilohertz for a 1 kilohertz total sweep.

By sweeping the frequency across 1 kilohertz, standing waves are reduced and the sound transmission to air is reduced by eliminating resonance problems. While the modulations is at 100 to 120 hertz in a sweep band of 1 kilohertz, the rate and band may be selected to minimize air-born noise and standing waves. A suitable frequency converter is sold by Swen Sonic, Inc. The isolation transformer 62 includes taps to permit either 120 or 240 volt operation.

To minimize noise received by a bather from the water, subharmonic vibrations caused by the sound generator are adjusted until a tolerable sound or no sound is perceived. This may be done by modifying the transducer or vibrating plate or plates to eliminate frequencies more easily perceived when transmitted through the bather's body. Moreover, sounds may be cancelled by transmitting to the bather sounds of the same subharmonic frequencies, such as through the water. This may be conveniently done by sensing the sound in the tub, filtering out the 30 KHz primary ultrasound and feeding the subharmonics back to the vibration plate transducer to cancel the subharmonics. Moreover, by using a much larger sweep in some configurations, noise received by the bather through the bather's body from the water may be reduced.

In FIG. 5, there is shown a block diagram of a circuit for receiving signals from the transducer 39 (FIG. 2) and providing a readout of the power density of the ultrasonic waves on the LED display 41. This circuit includes an amplifier 80, an analog-to-digital converter 82 and a display driver 84. These units by themselves are not part of the invention and one commercial unit is sold under the designations Linear Technology Operational Amplifier LT1014DN.

The operational amplifier is connected to cable 45 to receive signals representing the power density of the ultrasonic frequency, which it smooths and converts to a varying DC signal. Its output is electrically connected to the analog-to-digital converter 82 which converts the DC signal to a digital code for application to the display driver 84, which in turn drives the LED display 41 to indicate the power density in watts per square centimeter of the power of the ultrasonic sound in the body of water 18 (FIG. 2) received by the transducer 39 (FIG. 2). The amplifier 80 has a time constant which results in a DC output from the ultrasonic vibrations representing the total power impinging against the transducer 39 within the water 18 (FIG. 2). Instead of the analog-to-digital converter 82, the display driver 84 and the LED display 41, an oscilloscope may receive the analog signal and be used to tune the waveform by adjusting the D.C. bias to the ultrasonic generator 28 until no spikes are shown on the display screen of the oscilloscope.

In FIG. 6, there is shown a feedback circuit 90 connected between the output of the amplifier 80 (FIG. 5) and the input to the frequency converter 66 (FIG. 4) to control the power of the ultrasonic vibrations. It includes a threshold detector 92, a three-pole double-throw, relay operated switch 94, a warning lamp 96 and a flasher 98.

To protect against too large a power density, the threshold detector 92 is connected to receive signals from the output of the amplifier 80 through conductor 100 and has a first output electrically connected to the solenoid 102 of the three-pole double-throw, relay operated switch 94. With this connection, the threshold detector 92 energizes the solenoid 102 to throw the three-pole double-throw, relay operated switch 94 from its normal position in which the frequency converter 66 (FIG. 6) receives the full output from the autotransformer 64 shown in FIG. 6 to its energized position in which the frequency converter receives the output from tap 106 of the autotransformer 64 upon the detector 39 (FIG. 2) reaching a SPTP power density greater than 5.0 watts per square centimeter at 30 plus or minus 15 kilohertz, 100 Az, at 80 to 90 percent amplitude and a sweep rate of plus or minus 1 kilohertz.

The three-pole double-throw, relay operated switch 94 may be manually set to make contact with tap 106 on the autotransformer 64 to provide a reduced power to the frequency converter 66 for cleaning action or, in the alternative, to its antimicrobial position where the frequency converter 66 is directly connected across the autotransformer 64 at conductor 108 to receive full power. If the power exceeds the predetermined limit in the threshold detector 92, the relay coil 102 is energized to reswitch the three-pole double-throw, relay operated switch 94 back to the autotransformer tap 106, thus reducing power. If the power is not reduced, the threshold detector 92 applies signal to the three-pole double-throw, relay operated switch 94 and the flasher 98 to permit a manual reset of the three-pole double-throw, relay operated switch 94.

In FIG. 7, there is shown an elevational sectional view of the ultrasound transducer assembly 30 (FIG. 2) having a vibrating plate assembly 110 and a magnetostrictive vibrator assembly 112. The vibrating plate assembly 110 includes: (1) a glass-steel vibrating plate 40 in the preferred embodiment although an all stainless steel vibrating plate may be used; (2) an elastomeric seal 48; (3) a clamping collar 118; (4) a plurality of nickel laminations 120; and (5) a plurality of antivibration fasteners, one of which is shown at 122.

The plate 40 itself may be circular or rectangular having a thickness of approximately $\frac{1}{8}$ inch and an area enclosed within substantially an 8-inch diameter in the preferred embodiment. Its glass side is in contact with the interior and the glass side is fastened to the stainless steel plate. The stainless steel plate includes with nickel laminations. The size of the vibrating plate is determined by the need to transmit sufficient power through the water for the desired purposes such as hygienic, antimicrobial or therapeutic. Glass provides good coupling to the water, is inert, tough, electrically insulative, and easy to clean, however, other materials may be used.

The vibrating plate 40 should be larger than the opening in the tub wall if it directly contacts the body of water 18 (FIG. 2). Preferably it is sealed to the edge of a corresponding aperture in the tub 16, with the magnetostrictive vibrator being outside of the tub 16. To provide sealing on the inside of the tub 16 against escape of the body of water 18 (FIG. 2), the elastomeric seal 48 in the circular plate version is an annular gasket having an outer diameter of approximately 3 9/16 inches, an inner diameter of approximately 3¼ inches and a length of approximately 31/32 inch. It rests between a recessed circular shoulder of the tub 16 and the outer periphery of the vibrating plate 40, being pulled tightly against it to prevent leakage of fluid.

To hold the elastomeric seal 48 tightly between the vibrating plate 40 and the tub 16, an annular clamping collar 118 circumscribes the housing of the magnetostrictive vibrator assembly 112. The annular clamping collar 118 is of stainless steel and includes a plurality of circumferentially spaced-apart apertures each adapted to receive through it a corresponding one of a plurality of shanks of the fasteners 122 which circumscribe the annular clamping collar 118. In the preferred embodiment, the fasteners 122 are bolts having their heads fastened to the vibrating plate 40 in a circle with their shanks extending upwardly and their threaded portions passing through the corresponding holes in the annular clamping collar 118 at locations inward of the annular gasket 48 and approximately centered at a radius of $3\frac{1}{8}$ inches from the center of the annulus.

On the upper end of the shanks of the bolts are conventional external threads which receive a plurality of corresponding nuts in a manner to be described hereinafter to compress the annular clamping collar 118 and the vibrating plate 40 together between the annular gasket 48 and the wall of the tub 16. When held in this manner, the surface of the vibrating plate 40 that is in contact with the body of water 18 (FIG. 2) is flush with the inner surface of the tub 16, being recessed within a shoulder.

To vibrate the vibrating plate 40, the magnetostrictive vibrator assembly 112 includes a housing 130, a plurality of solenoid windings, two of which are shown at 132 and 134, and electrical connections to the solenoids extending through the housing (not shown in FIG. 7). The housing 130 is welded to the annular clamping collar 118 so that when the annular clamping collar 118 is clamped through the fasteners 122 to the vibrating plate 40, the ultrasound transducer assembly 30 is fastened to the tub 16 with the vibrating plate 40 in contact with the body of water 18 (FIG. 2) and the magnetostrictive elements positioned to vibrate the plate and electrically connected through cable 32 to the ultrasonic generator 28 (FIG. 2).

To vibrate the vibrating plate 40, the surface of the vibrating plate 40 adjacent to the coils such as 132 and 134 has fastened to it by adhesive, brazing or other means a plurality of the nickel laminations 120 spaced throughout the surface adjacent to the three solenoid windings (two of which are shown at 132 and 134) so that when the solenoid windings are energized at the operating frequency, which in the preferred embodiment is 30 kilohertz, the vibrating plate 40 transmits vibrations through the body of water 18 in a substantially uniform manner with a power density controllable by the power applied to the ultrasonic generator 28 (FIG. 2).

In the preferred embodiment, the vibrating plate includes a stainless steel plate to which nickel laminations are brazed and to which a toughened glass plate is fastened by expoxy. No conductive metal contacts the water and the stainless steel plate vibrates the glass plate. The glass plate is in contact with the water, seals the wall of the container and transmits vibrations to the water.

In FIG. 8, there is shown a plan view of the circular version of the ultrasound transducer assembly 30 with the top of the housing 130 and the solenoid coils such as those shown at 132 and 134 (FIG. 7) removed. As shown in this view, there are three fasteners 122A-122C each containing a corresponding nut 140A-140C threaded onto a corresponding shank 142A-142C to hold the vibrating plate 40 (FIG. 7) to the annular clamping collar 118 and thus hold the housing 130 onto tub 16 (FIG. 2). The cable 32 enters the housing 130 and is connected to a terminal block 144, to provide a ground connection at 146 to the vibrating plate 40 (FIG. 7) and electrical connections to three solenoids, mounted above 132, 134 and 136 to activate the nickel laminations 120 on the vibrating plate 40. With this embodiment, the three series connected solenoids simultaneously pull the nickel laminations 120 inwardly and release them outwardly to impart vibrations to the body of water 18.

Figure 9:
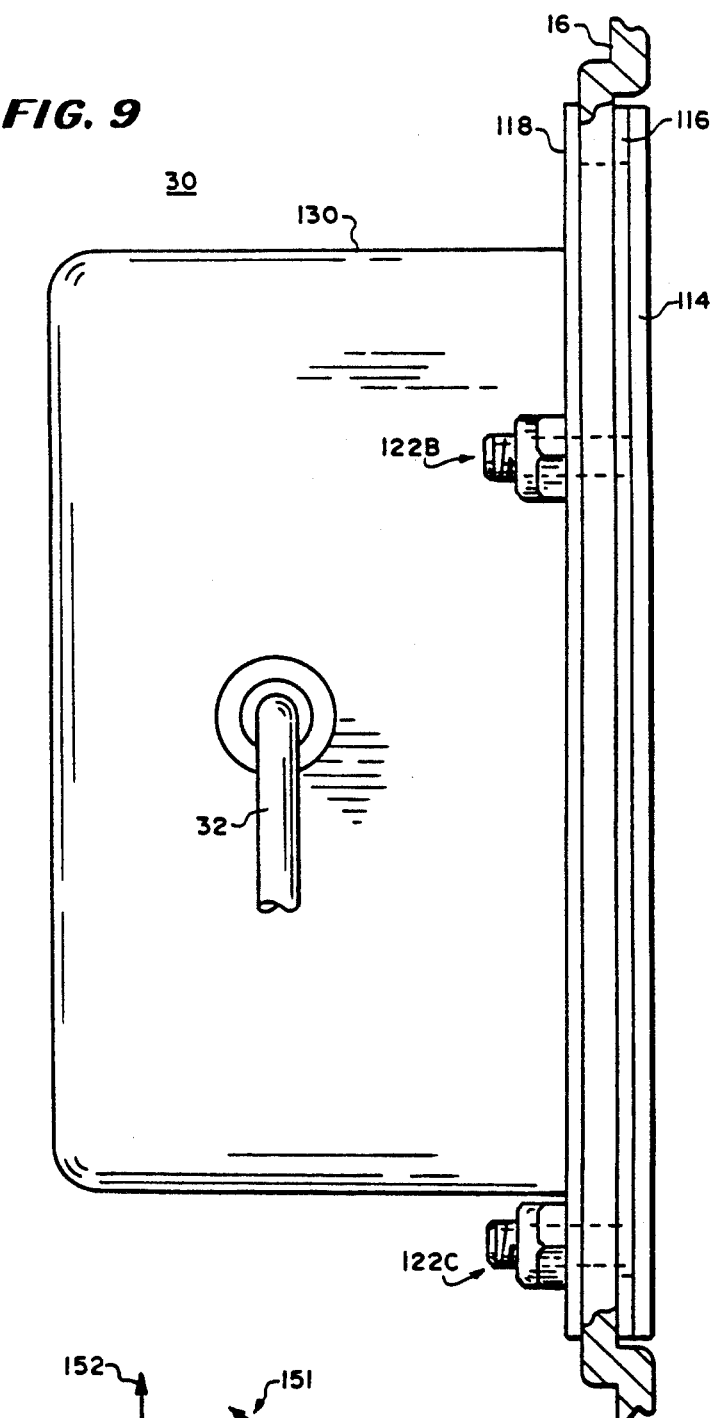
FIG. 9 is a side elevational view, partly broken away and sectioned, of the transducer element of FIG. 6.

In FIG. 9, there is shown a sectional view taken through the tub 16 to the side of the ultrasound transducer assembly 30 illustrating the manner in which the fasteners, two of which are shown at 122A and 122C. As shown in this view, the cable 32, which is a twisted and shielded conductor pair with a plastic covered sheath and elastomeric strain relief connection extends from the housing 130 to be connected to the ultrasonic generator 28 (FIG. 2). In an embodiment having the detector 39A (FIG. 7) bonded to the plate 40 (FIGS. 3 and 7), the cable 32 may contain the conductors 45 as well.

Figure 10:
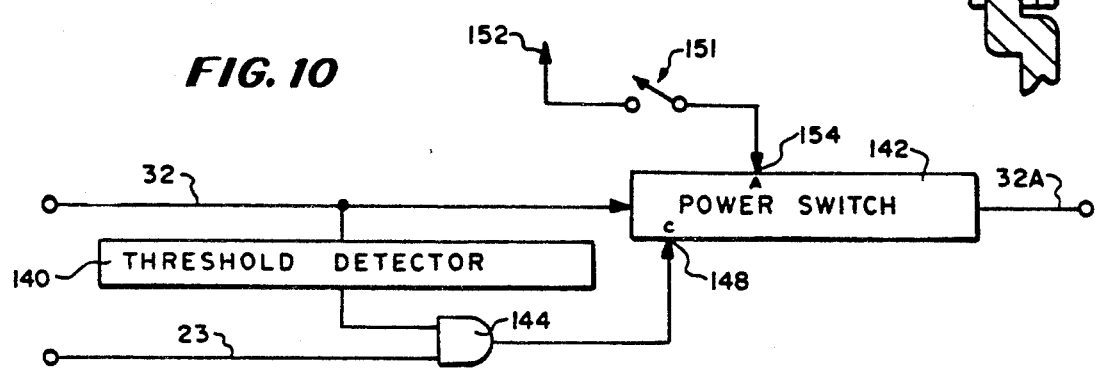
FIG. 10 is a block diagram of a control system which may be part of the bathing system of FIG. 2.

In FIG. 10 there is a block diagram of a circuit suitable for including in the control system 15 in circuit with cable 32 for the purpose of controlling the generation of ultrasonic waves including a threshold detector 140, a power switch 142 and an AND gate 144.

The power switch 142 has its input electrically connected to cable 32 to receive signals from the ultrasonic generator 28 (FIG. 2) and has its output electrically connected to the transducers 132, 134 and 136 (FIGS. 7 and 8) to apply oscillations to the transducers and thus transmit ultrasonic sound through the body of water 18 (FIG. 2). The power switch 142 may be a silicon controlled rectifier circuit, thyratron circuit or relay circuit which is normally closed to permit electrical signals to pass through it but capable of being opened by the application of a signal to a control input 148 and resetable by the application of a signal to a reset input terminal 154. Such circuits are well-known in the art.

To cause the power switch 142 to open, a threshold detector 140 has its input electrically connected to cable 32 and its output electrically connected to one of the inputs of a two-input AND gate 144. The other input of the AND gate 144 is electrically connected to conductor 23 and its output is electrically connected to the control input 148 of the power switch 142.

With this arrangement, when the signal on cable 32 is sufficient to cause ultrasonic vibrations at above 5 watts per square centimeter in the body of water 18 (FIG. 2), the threshold detector 140 applies a signal to one of the two inputs of the AND gate 144. If the body of water 18 now rises so that the sensor 17 (FIG. 2) senses the intrusion of a person into the tub, the detector 19 (FIG. 2) applies a signal through conductor 23 to the other input of the AND gate 144, causing the power switch 142 to receive a signal from the AND gate 144 and open. This terminates the signal to the transducers on cable 32A and thus the oscillations.

The control system 15 may be any type of capacitance detector. Such capacitance detectors are well-known in the field. Moreover, any other type of detector may be used to detect the intrusion or the proximity of an object to the body of water 18.

A reset switch 151 is electrically connected in series with a source of potential 152 and the reset input terminal 154 so that the ultrasound transducer assembly 30 may be reset by closing the reset switch 151 when the bathing system is again ready for operation. With this construction, an additional protection is provided against the accidental insertion into the bath of a person when high power is being applied for sterilization purposes.

Before being supplied to an end user, the transducer 39A (FIG. 7) is calibrated for the actual tub. This is done by measuring the power with a transducer located where the bather is expected to be and with a standard calibrated meter. The amplifier 80 (FIG. 5) is adjusted until the readout 41 (FIGS. 2 and 5) corresponds in its reading to the reading on the standard meter while the cable 45 is connected to the transducer 39A.

In operation, the operator fills the tub 16 with the body of water 18, adjusts the comfort controls for temperature and type of treatment and, after the patient is in the tub, energizes the arrangement to provide vibrations. The frequency and power density of the vibrations may be set in accordance with the purpose of the subunit. For example, cleaning may be performed at a lower power than antimicrobial treatment. The power may be changed during the bathing process so as, for example, to provide microbicidal activity at a first power density before the patient enters the tub and effective cleaning at a lower power density after the patient enters the tub.

To adjust the comfort level, the temperature of the water is controlled by the temperature control 37 (FIG. 2) as water flows from the faucet 26 (FIG. 2) until water has substantially filled the tub 16 or filled it to the desired level for treatment. The power density is then set by adjusting the dial 33 (FIG. 2), which adjusts the autotransformer 64 (FIG. 4).

To begin the treatment, the mains power switch 53 (FIG. 4) is closed which then applies power to the ground fault interrupter 55 and to the isolation transformer 62 so that the frequency converter 66 begins sweeping at its preset frequency, which normally will be 30 kilohertz with a 1 kilohertz sweep frequency. Although the frequency converter in the preferred embodiment is capable of providing up to 500 watts power, much lower powers are provided. The power is selected to result in the desired power density within the fluid by monitoring the fluid as the power is adjusted by the dial 37 (FIG. 2).

The power is monitored by measuring the power of the vibrations on the transducer 39 (FIG. 2) and transmitting signals representing this power to the amplifier 80 (FIG. 5) which amplifies it and transmits it to the analog-to-digital 82 (FIG. 5) converter which converts it to digital form and transmits it to the LED display 41 (FIG. 5).

To control the power, the dial 37 (FIG. 2) is turned generally until the power is in the range of 0.1 to 5.0 watts per square centimeter as read on the meter. The dial 37 moves the tap on the autotransformer 64 (FIG. 4) to control the voltage applied to the frequency converter 66. The power generated by the ultrasonic generator 28 is applied through the cable 32 to the ultrasound transducer assembly 30 (FIGS. 2, and 6–8) which results in vibrations being applied through the vibrating plate to the bath where they are applied to the patient and sensed by the transducer 39 (FIG. 2) . Generally, the power is applied for fifteen minutes or less and at a power and frequency which will not result in transient cavitation but yet to perform hygienic, antimicrobial or therapeutic treatment.

During use by a bather, some germicidal and fungicidal benefits are obtained by the low intensity ultrasound that is safe for the bather. This effect may be synergistically improved with additives that destroy pathogens and are brought into more ready contact with the pathogens by microstreaming induced by ultrasound.

During the inflamation period of wounds, the application of low frequency energy in the range of 15 to 100 kilohertz at intensities of between 1 and 5 watts per square centimeter promotes healing. The ultrasound is applied periodically such as for periods of between 5 minutes and 20 minutes at reasonable time intervals such as one or two times each day and results in reduced polymorphs indicating more effective action of the immune system or independent destruction of pathogens.

Similarly, during the rapid proliferation healing of wounds, periodic application of this ultrasound in substantially the same ultrasonic frequencies, intensities, time durations and number of repetitions each day promotes fiberblast development.

Because of these effects, it is possible to bathe animals or persons having wounds in a manner that aids in cleaning without damaging the wounds, and under some circumstances, even promoting healing. This is accomplished by immersing a bather with wounds for a number of times between once every two days and four times a day and for a time period selected to avoid increasing inflamation and retarding healing wherein the bather is cleaned while wound healing is aided. The number of times, time durations and repetition rate of bathing with sonically energized working fluid is selected by observing the wounds and reducing time in the ultrasound energized working fluid upon any one of irritation during bathing, increased inflammation after bathing or show healing rate.

If a ground fault is created, the current through the ground connection of the ground fault interrupter 55 (FIG. 4) causes it to open the circuit and terminate operation. Moreover, if the power density in the water 18 exceeds the amount set in the threshold detector 92 (FIG. 6), the relay solenoid 102 opens the circuit containing solenoid coil 57 (FIG. 4) through relay switch 61, causing the normally open mains power switch 53 to open. If this safety circuit fails, three-pole double-throw, relay operated switch 94 energizes warning lamp 96 and flasher 98 to provide an alarm.

In one embodiment, ultrasonic vibrations are applied at a power density of above 30 watts per square centimeter. In this embodiment, an additive is desirable, which may weaken cells walls of microbes or oxidize microbes. The ultrasonic vibrations at high power by themselves may sterilize the water and inanimate objects in it but the combination of additives for cleaning and further antiseptic reasons synergistically sterilze the water and, if desired, may clean and sterilize inanimate objects such as instruments and the like.

A detector in this embodiment detects the presence of a person or other object while the high power is being applied. For example, capacitance detectors may detect any time the water rises in the container. The detection will immediately de-energize or insert an attenuator in circuit with the ultrasonic generator to reduce the power density before damage can be done to a person who may accidentally enter the body of water.

When the water has been sterilized, in some embodiments such as those that are used for bathing or other treatment of animals, the power may be reduced to a level that is not irritating or damaging. The patient or other animal may then enter the bath and be subject to its cleaning action or other beneficial action from the bath without fear of contamination from the water.

One aspect of the invention is illustrated by the following examples:

EXAMPLES

The following examples illustrative the effect of ultrasound at 30 KHz on fungus, bacteria and virus in the absence of additives. The sound was applied to cultures in bags mounted in a tank in accordance with the invention. The power levels were determined according to a calibrated voltage meter as shown in Table 1. Concentrations were calculated according to formula 1.

TABLE 1

| Meter Setting | I(SPTP) | I(SPTA) | Specimen I(SATA) |
|---|---|---|---|
| 110 V AC | 2.5 W/cm$^2$ | 0.2 W/cm$^2$ | 0.1 W/cm$^2$ |
| 170 V AC | 5.5 W/cm$^2$ | 0.4 W/cm$^2$ | 0.3 W/cm$^2$ |

TABLE 1-continued

| Meter Setting | I(SPTP) | I(SPTA) | Specimen I(SATA) |
|---|---|---|---|
| 220 V AC | 11.3 W/cm$^2$ | 0.5 W/cm$^2$ | 0.4 W/cm$^2$ |

$$\text{Initial Concentration} = \frac{\text{\# of colonies}}{\text{vol. plated out.}} (x) \text{ dilution} \quad \text{Formula 1}$$

EXAMPLE 1

Fungus

1. Type: *Trichophyton mentagrophytes*
2. Procedure

*T. mentagrophytes* was grown at 26 degrees Centigrade on Emmon's modification of Sabouraud's agar (25 ml/plate). Agar plugs of one cm in diameter were taken from the fungal culture and transferred to a sterile Whirl-Pak (registered trademark) with 10 ml of sterile phosphate buffer at pH=7.0. After the treatments, the fungal plug was replated on the agar media stated above. One ml (milliliter) of the buffer was plated with the fungal plug to account for the fungal spores which may be lost during the period of time spent in the Whirl-Pak (registered trademark). This procedure was followed for the first experiment but was later modified for the subsequent experiments, whereby the plug was simply blotted on sterile filter paper to deter contaminants carried in the buffer, from being plated with the fungal plug. The plates were then incubated at 26 degrees Centigrade and ranked daily according to the amount of growth shown.

The amount of growth that appeared on plates was ranked in a grading from the least amount of growth to the greatest amount of growth. There were three sources of data to be reported. The exposed samples were those within the field of ultrasound exposure in the tub at 39 degrees Centigrade. Sham samples were placed in the same water (at 39 degrees Centigrade) but were placed beyond a barrier which protected them from exposure to ultrasound. Control samples remained at room temperature and never entered into the water.

3. Results:

Experiments suggested that ultrasound affected fungus growth. Two gave inconclusive results. In one experiment of the 15 specimens, all ultrasonic exposures were for a duration of 60 minutes, at either the 170 V AC or 220 V AC meter setting. All six of the exposed samples appeared in the lower growth gradings and all but one of the six shams were graded similarly to those of the three controls which were higher.

In another experiment, four out of the six exposed samples appeared in the two lower growth gradings five out of the six exposed samples appeared in the three lower growth gradings, but one sample that was exposed for 60 minutes at 220 V AC appeared in the grading of substantial growth. In still another experiment, of the twelve exposed samples, seven appeared in the three lowest growth gradings, and nine appeared in the four lowest growth gradings. However, three appeared in the grading of most growth attained.

EXAMPLE 2

Bacteria

1. Typies:

*Eschericia Coli (E. Coli)*
*Staphylococcus Aureus (S. aureus)*
*Bacillus Subtilis (B. subtilis)*
*Pseudomonas Fluorescens (P. fluorescens)*
*Pseudomonas Aeruginosa (P. aeruginosa)*

2. Procedure:

The procedure used to determine viability (survival capability) of the bacterial cells is the spread plate technique. The principle of the technique is that a certain volume (0.1 ml) of bacteria at a known concentration is pipetted out onto a sterile nutrient agar plate. The plates are incubated at 37 degrees Centigrade for a minimum of 24 hours. Any viable (living) cells grow on the agar into colonies and from these colonies, a concentration of viable cells/ml saline is obtained.

The bacteria remain in the broth until used in the experiment. The procedure is as follows:

The initial concentration is diluted with sterile normal saline. The cultures are diluted to a point where between 30–300 colonies/plate are obtained. This diluting is required in order to assure accurate counts of each colony.

After the proper dilution factor for each culture is determined, seven samples/culture are prepared. These seven samples are required for the different exposure conditions (Sham, 1, 2, 4, 8, 16, and 32 minutes). Each sample has a total of 10 ml/tube. Each sample is then transferred into sterile Whirl-Pak (registered trademark) bags and sealed, placed into the ultrasonic field and exposed. Each sample has three of its own sham plates (which receive no ultrasound exposure) to compare to the ultrasound exposed plates.

After exposure, three 0.1 ml plates are prepared for each sample and incubated at 37 degrees Centigrade for 24 hours. After incubation, the colonies that have grown are counted and compared to the results of the control plates.

A total of 39 experiments were conducted on 4 cultures of bacteria, at three meter settings, viz.,

| S. aureus: | 3 experiments at 220 V AC |
| | 6 experiments at 170 V AC |
| | 2 experiments at 110 V AC |
| P. aeruginosa: | 3 experiments at 220 V AC |
| | 5 experiments at 170 V AC |
| | 3 experiments at 110 V AC |
| E. coli: | 8 experiments at 170 V AC |
| | 3 experiments at 110 V AC |
| B. subtilis: | 3 experiments at 170 V AC |
| | 3 experiments at 110 V AC |

The meter settings were related to the ultrasonic exposure intensities as shown in Table 1.

For each meter setting for each bacteria, there were six exposure times (1, 2, 4, 8, 16 and 32 minutes) along with sham exposures. For each experiment, there are six individual plates for each exposure condition, 3 for shams and 3 for exposed. These plate counts are then averaged and computed into formula 1 to determine the cell concentration and to develop the graph of percent killed relative to the control.

3. Results:

The results are shown in Tables 2–5. There is a clear trend of greater kill as the exposure time is increased. There is also a difference in the kill rate as a function of bacteria type.

TABLE 2

| | Percentage Killed S. aureus | | |
| Exposure Time | 220 V | 170 V | 110 V |
| --- | --- | --- | --- |
| 32 minutes | 54.8% | 48.6% | 18.0% |
| 16 minutes | 11.1% | 37.4% | 11.7% |
| 8 minutes | 30.0% | 26.3% | 19.3% |
| 4 minutes | 9.4% | 28.3% | 15.7% |
| 2 minutes | 25.0% | 27.7% | 13.0% |
| 1 minute | 28.6% | 28.8% | 26.4% |

220 V setting 3 experiments
170 V setting 6 experiments
110 V setting 2 experiments

TABLE 3

| | Percentage Killed P. aeruginosa | | |
| Exposure Time | 220 V | 170 V | 110 V |
| --- | --- | --- | --- |
| 32 minutes | 90.0% | 61.4% | 66.7% |
| 16 minutes | 84.5% | 59.9% | 42.6% |
| 8 minutes | 60.4% | 39.4% | 22.4% |
| 4 minutes | 66.7% | 38.8% | 15.0% |
| 2 minutes | 73.0% | 54.1% | 33.8% |
| 1 minute | 84.4% | 17.2% | 14.4% |

220 V setting 3 experiments
170 V setting 5 experiments
110 V setting 3 experiments

TABLE 4

| | Percentage Killed E. coli | | |
| Exposure Time | 220 V | 170 V | 110 V |
| --- | --- | --- | --- |
| 32 minutes | N | 32.7% | 40.0% |
| 16 minutes | O | 19.6% | 8.9% |
| 8 minutes | D | 13.9% | 24.0% |
| 4 minutes | A | 25.3% | 7.7% |
| 2 minutes | T | 15.2% | 19.6% |
| 1 minute | A | 21.8% | 18.2% |

220 V setting 0 experiments
170 V setting 8 experiments
110 V setting 3 experiments

TABLE 5

| | Percentage Killed B. subtilis | | |
| Exposure Time | 220 V | 170 V | 110 V |
| --- | --- | --- | --- |
| 32 minutes | N | 76.1% | 8.8% |
| 16 minutes | O | 78.1% | 6.1% |
| 8 minutes | D | 73.1% | 17.7% |
| 4 minutes | A | 59.0% | 11.3% |
| 2 minutes | T | 40.2% | 0.0% |
| 1 minute | A | 36.3% | 0.0% |

220 V setting 0 experiments
170 V setting 3 experiments
110 V setting 3 experiments The most difficult bacteria to kill appears to be *E. coli* and the easiest to kill is *B. subtilis*.

Evaluating the two bacteria, *S. aureus* and *P. aeruginosa*, for which there are data at all three meter settings suggests the following. A much greater ultrasonic intensity would be required to kill substantially all of the *S. aureus* than that for *P. aeruginosa*. It appears that the kill rate is about one-half to one-third for *S. aureus* as compared with *P. aeruginosa*. Given the fact that extrapolating outside of the available data range is subject to many problems, it would appear that a doubling of the intensity from the 220 V AX meter setting for *P. aeruginosa* might substantially kill most of this bacteria. Therefore, based upon energy considerations, an addition two to three times in intensity would be required for substantial kill of *S. aureus*.

EXAMPLE 3

1. Types:
*Feline Herpesvirus* type 1 (FVH-1)
*Feline calicivirus*

2. Procedure

Two analytical procedures were employed to determine the effect of an ultrasonic field on virus viability (survival), viz., infectivity and structural integrity.

Ten-fold dilutions of the source viruses are made in maintenance media. A dilution is then transferred into 2 sterile Whirl-Pak (registered trademark) bags (10 ml/bag), one exposed or treated sample and one control or unexposed sample. The samples are kept at 4 degrees Centigrade before and after ultrasound exposure. Controls are kept at the same temperature (39 degrees Centigrade) as the exposed samples for the duration of the treatment.

The amount (titer) of the infectious virus in a sample prior to and after treatment (ultrasound exposure) is measured by a virus microtitration procedure for $TCID_{50}$ (50 percent tissue culture infectious dose) end point determination. After exposure, logarithmic dilutions of each exposed and control sample as well as the original sample dilution (back titration) are made in maintenance media. Each dilution is then added in an appropriate volume to 4 wells of a 96-well cell culture plate.

The inoculated cultures are incubated 37 degrees Centigrade in a 5 percent $CO_2$ atmosphere environment for five days. If the cells in the inoculated well show a specific viral cytopathic effect (CPE), then it is considered positive (infected). The end point is determined from the highest dilution which produced a CPE in 50 percent of the cell cultures inoculated based on the calculation method of Reed and Muench (Am. J. Hygiene 27(3): 493-497, 1938).

The structural integrity of ultrasonic exposed virus compared to nonexposed virus is evaluated by imaging the virus with negative staining electron microscopy. The threshold of detection for virus by this procedure is a final virus titer in the sample of greater than $10^4$ $TCID_{50}$/ml. Virus from 5 ml of each sample is pelleted by ultracentrifugation. The virus particles in the pellet are then suspended in distilled water, an aliquot of which is stained with 1 percent phosphotungstic acid and placed on Forvar carbon-coated grids.

The criterion used to group viruses into families are the nature of the genome (DNA or RNA, double or single strand, segmented or nonsegmented), the biochemical characteristics (such as viral specified enzymes), and the morphology of the viron (the original classification scheme). Physical disruption of the virion structure (morphology) abrogates viral infectivity. The primary focus of this section of the study is to determine the effect of an ultrasonic field on viral viability as measured by viral infectivity.

Because of this focus, viruses used were chosen based on their morpho logy, enveloped or nonenveloped, and to represent a viral family that either contains or has similar structure to a human virus of interest. The particular viruses chosen were *Feline herpesvirus* which is of the same subfamily as human herpes simplex virus type 1 and 2 and *Feline calicivirus* which has similar morphology to the Picornaviridae family which contains human enteric viruses (i.e., poliovirus). Human viruses can be used once successful viral inactivation ultrasonic parameters are established.

TABLE 6

| Sample | | Titer ($TCID_{50}$/ml) | Negative Staining EM* |
|---|---|---|---|
| 1. Back titration | | $2.4 \times 10^4$ | No virus seen |
| 2. FHV 30/exp. | 39 degrees C. | $7.2 \times 10^2$ | No virus seen |
| 3. FHV 30/sham | 39 degrees C. | $2.2 \times 10^4$ | No virus seen |
| 4. FHV 60/exp. | 39 degrees C. | $2.2 \times 10^1$ | No virus seen |
| 5. 60/sham | 39 degrees C. | $1.3 \times 10^4$ | No virus seen |

*Limits of detection by negative staining EM fall in the range of $10^4$ to $10^5$ $TCID_{50}$/ml.

3. Results:

The results are shown in Table 6.
Virus Results:

A total of 18 virus experiments have been performed, twelve with feline herpesvirus type 1 (FHV) and six with the feline calicivirus (FCV). The virus was titered and put into sterile Whirl-Pak (registered trademark) bags then transported at 4 degrees Centigrade to the tub.

For experiments 1-5 (Tables 6-10), there were two exposure times (30 and 60 minutes), both at a meter setting of 170 V AC for FHV. For experiments 6-12 (Tables 11-17), there was one exposure condition (60 minutes at a meter setting of 170 V AC) for FHV. For experiments 13-16 (Tables 18-21), there was one exposure condition (60 minutes at a meter setting of 170 V AC) and for experiments 17-18 (Tables 22 and 23), also one exposure condition (60 minutes at a meter setting of 220 V AC), for FCV. All experiments included appropriate controls (called back titration) and sham (virus placed in bath without being exposed to sound).

For the first two experiments, the virus was analyzed for both structural integrity and infectivity. It was concluded that the structural integrity integrity analysis did not provide useful information and thus was not included for subsequent experiments where only infectivity analysis was performed.

TABLE 7

Experiment 2
10 ml/bag
Titer used: $10^6$ $TCID_{50}$/ml

| Sample | | Titer ($TCID_{50}$/ml) | Negative Staining EM* |
|---|---|---|---|
| 1. Back titration | | $7.2 \times 10^5$ | Virus and nucleocapsid seen |
| 2. FHV 30/exp. | 39 degrees C. | $7.2 \times 10^5$ | Virus and nucleocapsid seen |
| 3. FHV 30/sham | 39 degrees C. | $4 \times 10^5$ | Virus and nucleocapsid seen |
| 4. FHV 60/exp. | 39 degrees C. | $4 \times 10^5$ | Virus and nucleocapsid seen |
| 5. FHV 60/sham | 39 degrees C. | $7.2 \times 10^5$ | Virus and nucleocapsid seen |

*Limits of detection by negative staining EM fall in the range of $10^4$ to $10^5$ $TCID_{50}$/ml.

TABLE 8

Experiment 3
10 ml/bag
Titer used: $10^6$ $TCID_{50}$/ml

| | Titer ($TCID_{50}$/ml) |
|---|---|
| 1. Back titration | $2.6 \times 10^5$ |

TABLE 8-continued

Experiment 3
10 ml/bag
Titer used: $10^6$ TCID$_{50}$/ml

| | | Titer (TCID$_{50}$/ml) |
|---|---|---|
| 2. FHV 30/exp. | 39 degrees C. | $4.0 \times 10^5$ |
| 3. FHV 30/sham | 39 degrees C. | $4.0 \times 10^5$ |
| 4. FHV 60/exp. | 39 degrees C. | $2.2 \times 10^5$ |
| 5. FHV 60/sham | 39 degrees C. | $2.2 \times 10^5$ |

TABLE 9

Experiment 4
10 ml/bag
Titer used: $10^4$ and $10^5$ TCID$_{50}$/ml

| | | Titer (TCID$_{50}$/ml) |
|---|---|---|
| $10^5$ | | |
| 1. Back titration | | $4.7 \times 10^5$ |
| 2. FHV 30/exp. | 39 degrees C. | $2.2 \times 10^5$ |
| 3. FHV 30/sham | 39 degrees C. | $4.0 \times 10^5$ |
| 4. FHV 60/exp. | 39 degrees C. | $2.2 \times 10^5$ |
| 5. FHV 60/sham | 39 degrees C. | $4.0 \times 10^5$ |
| $10^4$ | | |
| 6. Back titration | | $4.0 \times 10^4$ |
| 7. FHV 30/exp. | 39 degrees C. | $4.0 \times 10^4$ |
| 8. FHV 30/sham | 39 degrees C. | $2.2 \times 10^4$ |
| 9. FHV 60/exp. | 39 degrees C. | $2.2 \times 10^1$ |
| 10. FHV 60/sham | 39 degrees C. | $2.2 \times 10^4$ |

TABLE 10

Experiment 5
10 ml/bag
Titer used: $10^4$ and $10^5$ TCID$_{50}$/ml

| | | Titer (TCID$_{50}$/ml) |
|---|---|---|
| $10^5$ | | |
| 1. Back titration | | $5.6 \times 10^4$ |
| 2. FHV 30/exp. | 39 degrees C. | $1.3 \times 10^5$ |
| 3. FHV 30/sham | 39 degrees C. | $1.3 \times 10^5$ |
| 4. FHV 60/exp. | 39 degrees C. | $2.2 \times 10^5$ |
| 5. FHV 60/sham | 39 degrees C. | $7.2 \times 10^4$ |
| $10^4$ | | |
| 6. Back titration | | $1.2 \times 10^5$ |
| 7. FHV 30/exp. | 39 degrees C. | $2.2 \times 10^3$ |
| 8. FHV 30/sham | 39 degrees C. | $7.2 \times 10^3$ |
| 9. FHV 60/exp. | 39 degrees C. | 0 |
| 10. FHV 60/sham | 39 degrees C. | $4.0 \times 10^4$ |

TABLE 11

Experiment 6
10 ml/bag
A = sonicated source virus*
B = nonsonicated source virus*
Titer used: $10^5$ and $10^4$ TCID$_{50}$/ml)

| | | Titer (TCID$_{50}$/ml) |
|---|---|---|
| A $10^5$ | | |
| 1. Back titration | | $4.0 \times 10^5$ |
| 2. FHV 60/exp. | 39 degrees C. | $7.2 \times 10^5$ |
| 3. FHV 60/sham | 39 degrees C. | $7.2 \times 10^5$ |
| B $10^5$ | | |
| 4. Back titration | | $4.0 \times 10^5$ |
| 5. FHV 60/exp. | 39 degrees C. | $2.2 \times 10^5$ |
| 6. FHV 60/sham | 39 degrees C. | $4.0 \times 10^5$ |
| A $10^4$ | | |
| 7. Back titration | | $2.2 \times 10^5$ |
| 8. FHV 60/exp. | 39 degrees C. | $4.0 \times 10^2$ |
| 9. FHV 60/sham | 39 degrees C. | $7.2 \times 10^4$ |
| B $10^4$ | | |
| 10. Back titration | | $7.2 \times 10^4$ |
| 11. FHV 60/exp. | 39 degrees C. | $7.2 \times 10^1$ |

TABLE 11-continued

Experiment 6
10 ml/bag
A = sonicated source virus*
B = nonsonicated source virus*
Titer used: $10^5$ and $10^4$ TCID$_{50}$/ml)

| | | Titer (TCID$_{50}$/ml) |
|---|---|---|
| 12. FHV 60/sham | 39 degrees C. | $1.3 \times 10^2$ |

*The sonication referred to here is not from the 26 kHz source of the tub. This sonication was for the purpose of studying the aggregation phenomena. This sonication did not affect the aggregation phenomena.

TABLE 12

Experiment 7
10 ml/bag
All sonications done for 60 minutes at 39 degrees Centigrade

| | Titer (TCID$_{50}$/ml) |
|---|---|
| $10^5$ | |
| 1. Back titration | $7.2 \times 10^5$ |
| 2. FHV exp. | $4.0 \times 10^5$ |
| 3. FHV sham | $1.28 \times 10^6$ |
| $10^4$ | |
| 4. Back titration | $2.24 \times 10^5$ |
| 5. FHV exp. | $2.24 \times 10^4$ |
| 6. FHV sham | $4.0 \times 10^4$ |
| $10^3$ | |
| 7. Back titration | $7.2 \times 10^3$ |
| 8. FHV exp. | $2.24 \times 10^3$ |
| 9. FHV sham | $2.24 \times 10^3$ |
| $10^2$ | |
| 10. Back titration | $4.0 \times 10^2$ |
| 11. FHV exp. | 0 |
| 2. FHV sham | $4.0 \times 10^2$ |

TABLE 13

Experiment 8
10 ml/bag
All sonications done for 60 minutes at 39 degrees Centigrade

| | Titer (TCID$_{50}$/ml) |
|---|---|
| $10^5$ | |
| 1. Back titration | $1.28 \times 10^6$ |
| 2. FHV exp. | $4.0 \times 10^5$ |
| 3. FHV sham | $2.24 \times 10^5$ |
| $10^4$ | |
| 4. Back titration | $1.28 \times 10^5$ |
| 5. FHV exp. | $1.28 \times 10^3$ |
| 6. FHV sham | $1.28 \times 10^4$ |
| $10^3$ | |
| 7. Back titration | $2.24 \times 10^4$ |
| 8. FHV exp. | 0 |
| 9. FHV sham | $2.24 \times 10^3$ |

TABLE 14

Experiment 9
10 ml/bag
All sonications done for 60 minutes at 39 degrees Centigrade

| | Titer (TCID$_{50}$/ml) |
|---|---|
| $10^4$ | |
| 1. Back titration | $7.2 \times 10^4$ |
| 2. FHV exp. | 0 |
| 3. FHV sham | $1.28 \times 10^4$ |
| $10^3$ | |
| 4. Back titration | $7.2 \times 10^3$ |
| 5. FHV exp. | $2.2 \times 10^1$ |
| 6. FHV sham | $2.24 \times 10^3$ |
| $10^2$ | |
| 7. Back titration | $7.2 \times 10^2$ |
| 8. FHV exp. | $2.2 \times 10^1$ |
| 9. Sham | $2.24 \times 10^2$ |

TABLE 15

Experiment 10
10 ml/bag
All sonications done for 60 minutes at 39 degrees Centigrade

| | Titer (TCID$_{50}$/ml) |
|---|---|
| $10^4$ | |
| 1. Back titration | $4.0 \times 10^3$ |
| 2. FHV exp. | $4.0 \times 10^3$ |
| 3. FHV sham | $7.2 \times 10^3$ |
| $10^3$ | |
| 4. Back titration | $1.28 \times 10^2$ |
| 5. FHV exp. | 0 |
| 6. FHV sham | $2.24 \times 10^3$ |
| $10^2$ | |
| 7. Back titration | 0 |
| 8. FHV exp. | 0 |
| 9. FHV sham | 0 |

TABLE 16

Experiment 11
10 ml/bag
All sonications done for 60 minutes at 39 degrees Centigrade

| | Titer (TCID$_{50}$/ml) |
|---|---|
| $10^4$ | |
| 1. Back titration | $7.2 \times 10^4$ |
| 2. FHV exp. | $2.24 \times 10^4$ |
| 3. FHV sham | $2.24 \times 10^4$ |
| $10^3$ | |
| 4. Back titration | $7.2 \times 10^2$ |
| 5. FHV exp. | 0 |
| 6. FHV sham | $7.2 \times 10^2$ |
| $10^2$ | |
| 7. Back titration | $4.0 \times 10^2$ |
| 8. FHV exp. | 0 |
| 9. FHV sham | 0 |

TABLE 17

Experiment 12
10 ml/bag
All sonications done for 60 minutes at 39 degrees Centigrade

| | Titer (TCID$_{50}$/ml) |
|---|---|
| $10^4$ | |
| 1. Back titration | $2.24 \times 10^4$ |
| 2. FHV exp. | 0 |
| 3. FHV sham | $1.28 \times 10^4$ |
| $10^3$ | |
| 4. Back titration | $4.0 \times 10^2$ |
| 5. FHV exp. | 0 |
| 6. FHV sham | $7.2 \times 10^2$ |
| 7. Back titration | $7.2 \times 10^1$ |
| 8. FHV exp. | 0 |
| 9. FHV sham | 0 |

TABLE 18

Experiment 13
10/ml bag
All sonications done for 60 minutes at 39 degrees Centigrade

| | Titer (TCID$_{50}$/ml) |
|---|---|
| $10^5$ | |
| 1. Back titration | $4.0 \times 10^4$ |
| 2. FCV exp. | $7.2 \times 10^3$ |
| 3. FCV sham | $1.28 \times 10^4$ |
| $10^4$ | |
| 4. Back titration | $2.24 \times 10^3$ |
| 5. FCV exp. | $4.0 \times 10^2$ |
| 6. FCV sham | $7.2 \times 10^2$ |
| $10^3$ | |
| 7. Back titration | $2.24 \times 10^2$ |
| 8. FCV exp. | $2.24 \times 10^1$ |
| 9. FCV sham | $7.2 \times 10^1$ |
| $10^2$ | |
| 10. Back titration | 0 |
| 11. FCV exp. | 0 |
| 12. FCV sham | 0 |

TABLE 19

Experiment 14
10 ml/bag
All sonications done for 60 minutes at 39 degrees Centigrade

| | Titer (TCID$_{50}$/ml) |
|---|---|
| $10^5$ | |
| 1. Back titration | $1.28 \times 10^5$ |
| 2. FCV exp. | $1.28 \times 10^5$ |
| 3. FCV sham | $4.0 \times 10^4$ |
| $10^4$ | |
| 4. Back titration | $2.24 \times 10^4$ |
| 5. FCV exp. | $7.2 \times 10^3$ |
| 6. FCV sham | $4.0 \times 10^3$ |
| $10^3$ | |
| 7. Back titration | $2.24 \times 10^3$ |
| 8. FCV exp. | $1.28 \times 10^2$ |
| 9. FCV sham | $1.28 \times 10^2$ |
| $10^2$ | |
| 10. Back titration | $4.0 \times 10^2$ |
| 11. FCV exp. | $2.24 \times 10^1$ |
| 12. FCV sham | 0 |

TABLE 20

Experiment 15
10 ml/bag
All sonications done for 60 minutes at 39 degrees Centigrade

| | Titer (TCID$_{50}$/ml) |
|---|---|
| $10^5$ | |
| 1. Back titration | $4.0 \times 10^5$ |
| 2. FCV exp. | $1.28 \times 10^4$ |
| 3. FCV sham | $7.2 \times 10^4$ |
| $10^4$ | |
| 4. Back titration | $4.0 \times 10^4$ |
| 5. FCV exp. | $2.24 \times 10^3$ |
| 6. FCV sham | $1.28 \times 10^4$ |
| $10^3$ | |
| 7. Back titration | $1.28 \times 10^3$ |
| 8. FCV exp. | $2.24 \times 10^2$ |
| 9. FCV sham | $2.24 \times 10^2$ |
| $10^2$ | |
| 10. Back titration | $4.0 \times 10^2$ |
| 11. FCV exp. | $7.2 \times 10^1$ |
| 12. FCV sham | $2.24 \times 10^1$ |

TABLE 21

Experiment 16
10 ml/bag
All sonications done for 60 minutes at 39 degrees Centigrade

| | Titer (TCID$_{50}$/ml) |
|---|---|
| $10^5$ | |
| 1. Back titration | $1.28 \times 10^5$ |
| 2. FCV exp. | $7.2 \times 10^4$ |
| 3. FCV sham | $7.2 \times 10^4$ |
| $10^4$ | |
| 4. Back titration | $7.2 \times 10^3$ |
| 5. FCV exp. | $4.0 \times 10^3$ |
| 6. FCV sham | $1.28 \times 10^4$ |
| $10^3$ | |
| 7. Back titration | $1.28 \times 10^3$ |
| 8. FCV exp. | 0 |
| 9. FCV sham | $4.0 \times 10^2$ |
| $10^2$ | |

TABLE 21-continued

Experiment 16
10 ml/bag
All sonications done for 60 minutes at 39 degrees Centigrade

| | Titer (TCID$_{50}$/ml) |
|---|---|
| 10. Back titration | $2.24 \times 10^2$ |
| 11. FCV exp. | 0 |
| 12. FCV sham | $4.0 \times 10^1$ |

TABLE 22

Experiment 17
10 ml/bag
All sonications done for 60 minutes at 39 degrees Centigrade

| | Titer (TCID$_{50}$/ml) |
|---|---|
| 1. Back titration | $7.2 \times 10^5$ |
| 2. FCV exp. | $1.28 \times 10^5$ |
| 3. FCV sham | $2.24 \times 10^5$ |
| $10^4$ | |
| 4. Back titration | $2.24 \times 10^4$ |
| 5. FCV exp. | $7.2 \times 10^3$ |
| 6. FCV sham | $2.24 \times 10^4$ |
| $10^3$ | |
| 7. Back titration | $4.0 \times 10^3$ |
| 8. FCV exp. | $1.28 \times 10^2$ |
| 9. FCV sham | $2.24 \times 10^3$ |
| $10^2$ | |
| 10. Back titration | $2.24 \times 10^2$ |
| 11. FCV exp. | $4.0 \times 10^1$ |
| 12. FCV sham | $4.0 \times 10^2$ |

TABLE 23

Experiment 18
10 ml/bag
All sonications done for 60 minutes at 39 degrees Centigrade

| | Titer (TCID$_{50}$/ml) |
|---|---|
| 1. Back titration | $1.28 \times 10^6$ |
| 2. FCV exp. | $4.0 \times 10^4$ |
| 3. FCV sham | $4.0 \times 10^5$ |
| $10^4$ | |
| 4. Back titration | $1.28 \times 10^5$ |
| 5. FCV exp. | $7.2 \times 10^3$ |
| 6. FCV sham | $7.2 \times 10^4$ |
| $10^3$ | |
| 7. Back titration | $7.2 \times 10^3$ |
| 8. FCV exp. | $2.24 \times 10^3$ |
| 9. FCV sham | $7.2 \times 10^2$ |
| $10^2$ | |
| 10. Back titration | $7.2 \times 10^2$ |
| 11. FCV exp. | $1.28 \times 10^2$ |
| 12. FCV sham | $1.28 \times 10^2$ |

Viral Structural Integrity

Negative staining electron microscopy was used to visualize the virions in the treated, sham and back titration samples for Experiments 1 and 2 (enveloped virus). Significant differences were not apparent. This result may in part be due to an aggregation phenomenon that occurs at virus titers necessary for the limits of detection by this technique, that is, a titer $10^4$ to $10^5$ TCID$_{50}$/ml (see Viral Infectivity, Experiments 1-6 for discussion of the aggregation phenomenon problem).

Viral Infectivity

Enveloped Virus (FHV-1)

1. Experiments 1-6

A titer of $10^5$ TCIV 50/ml appeared to be the critical infectious unit number at which viral aggregation is most evident. Such a viral aggregate is measured as one infectious unit. This aggregation phenomenon protects the more internal virions from the inactivating effects of the ultrasound. Therefore, since all virions within an aggregate must be inactivated to destroy the infectivity of an aggregate, the virus titer was not measurably reduced by treatment. Therefore, subsequent experiments used titers less than or equal to $10^5$ TCID$_{50}$/ml.

2. Experiments 7-12 (FHV)

The ultrasonic exposure conditions used (170 V AC meter setting for 60 minutes at 39 degrees Centigrade) resulted in significant reduction of infectivity of samples containing a titer $10^4$ TCID$_{50}$/ml. Virions in samples containing titer of $10^2$ TCID$_{50}$/ml were more liable to environmental conditions (such as temperature and light), therefore, were easily inactivated.

3. Experiment 13-16 (FCV)

The ultrasonic exposure conditions were the same as for experiments 7-12. Results indicate that such conditions did not significantly reduce viral infectivity.

4. Experiment 17 and 18 (FCV)

The higher ultrasonic exposure conditions (220 V AC meter setting for 60 minutes) showed that the virus was not significantly reduced.

CONCLUSION

The experimental conditions used significantly reduced viral infectivity of the lower titered enveloped virus (FHF) samples. However, the nonenveloped virus (FCV) was refractive to the inactivating effects of the ultrasound. This reflects the fact that enveloped viruses are more liable to environmental influences than are nonenveloped viruses.

The enveloped virus consists of a lipid/protein bilayer membrane (the envelope). Disruption of the envelope generally kills this virus type. To kill the nonenveloped type virus (FCV) requires disruption or distruction of the nucleocapsid. More energy is required to destroy the nucleocapsid than disrupt the envelope. The findings herein are consistent with this observation.

The experiments indicate the ability of 30 KHz ultrasound to destroy microbes in amounts related to the time of radiation and intensity of the ultrasound. This indicates the ability to sterilize with or without additives. The killing intensity can be obtained by increasing power until samples in bags are completely destroyed.

From the above description, it can be understood that the apparatus and method of this invention has several advantages over the prior art, such as: (1) it has hygienic, therapeutic and antimicrobial benefits while being harmless to animals; (2) it makes economical use of vibrating transducers by avoiding standing waves and using low attenuation water as a working fluid; and (3) performs both cleaning and healing benefits while at the same time provide antiviral, antibacterial and antifungal activity in a manner making it suitable for treatment of certain particularly severe maladies such as treating patients with severe burns.

Although a preferred embodiment of the invention has been described with some particularity, many modifications and variations in the invention are possible within the light of the above teachings. Therefore, it is to be understood, that within the scope of the appended claims, the invention m ay be practiced other than as specifically described.

What is claimed is:

1. A method of making ultrasonic apparatus for the treatment of animals comprising the steps of:
   forming a container adapted to hold sufficient working fluid to reach a predetermined depth between the top surface of the working fluid and the lowest point in the working fluid;

mounting to said container at least one vibrator for applying ultrasonic vibrations to the working fluid in a frequency range of between 15 kilohertz and 100 kilohertz at power densities measuring at least over a portion of the range between 0.1 and 30 watts per square centimeter at a location in said container below the top surface of the working fluid;

putting working fluid in the container;

sensing body borne audible sound through the working fluid in the container; and adjusting the ultrasonic apparatus to reduce undesirable body borne audible sound by attenuating subharmonic application to the working fluid until the sensed body borne audible sound is improved.

2. A method according to claim 1 in which the step of sensing the body borne audible sound includes the step of inserting at least a portion of the body in the working fluid whereby sound is heard at a pitch different than airborne sound in a vicinity of the ultrasonic apparatus.

3. A method according in claim 1 further including the step of driving the vibrator with a plurality of transducers; the step of adjusting the apparatus including the steps of adjusting at least the shape of one vibrator in the container, the size of at least one vibrator and an arrangement of transducers driving a vibrator.

4. A method according to claim 1 in which the step of adjusting the apparatus includes the steps of electrically sensing subharmonics in the working fluid; generating electrical signals corresponding to the subharmonics and subtracting the electrical signals from signals energizing at least one vibrator.

5. A method according to claim 1 in which the step of adjusting the apparatus includes the steps of altering at least one of the number of the vibrators, the location of at least one of the plurality of vibrators, altering the size of at least one of the plurality of vibrators, altering the size of the container, altering the shape of the container, baffling for at least some of the plurality of vibrators and changing a material of which the container is made to provide reduced undesirable audible noise.

6. A method according to claim 1 in which the step of mounting to said container at least one vibrator includes the step of mounting a glass plate within the wall of said container and mounting an electronic transducer positioned to vibrate the glass plate, whereby vibrations are transmitted by the glass plate to the working fluid.

* * * * *